(12) United States Patent
Löwenhielm et al.

(10) Patent No.: US 9,492,549 B2
(45) Date of Patent: Nov. 15, 2016

(54) ANTIMICROBIAL GELS

(75) Inventors: Peter Löwenhielm, Täby (SE); Malin Holmén, Göteborg (SE); Dennis Hansson, Gunnilse (SE); Sofia Bergstrand, Kungsbacka (SE); Stefan Areskoug, Göteborg (SE)

(73) Assignee: Mölnlycke Health Care AB, Göteborg (SE)

( * ) Notice: Subject to any disclaimer, the term of this patent is extended or adjusted under 35 U.S.C. 154(b) by 116 days.

(21) Appl. No.: 13/640,652

(22) PCT Filed: Apr. 13, 2011

(86) PCT No.: PCT/SE2011/050452
§ 371 (c)(1),
(2), (4) Date: Jan. 10, 2013

(87) PCT Pub. No.: WO2011/129759
PCT Pub. Date: Oct. 20, 2011

(65) Prior Publication Data
US 2013/0101633 A1    Apr. 25, 2013

Related U.S. Application Data

(60) Provisional application No. 61/323,926, filed on Apr. 14, 2010.

(30) Foreign Application Priority Data

Apr. 14, 2010  (SE) ..................... 1050367

(51) Int. Cl.
| | |
|---|---|
| A61L 15/26 | (2006.01) |
| A61K 47/38 | (2006.01) |
| A61K 47/10 | (2006.01) |
| A61L 15/46 | (2006.01) |
| A61L 26/00 | (2006.01) |

(52) U.S. Cl.
CPC .............. *A61K 47/38* (2013.01); *A61K 47/10* (2013.01); *A61L 15/26* (2013.01); *A61L 15/46* (2013.01); *A61L 26/0019* (2013.01); *A61L 26/0066* (2013.01); *A61L 2300/104* (2013.01); *A61L 2300/404* (2013.01)

(58) Field of Classification Search
None
See application file for complete search history.

(56) References Cited

U.S. PATENT DOCUMENTS

| | | |
|---|---|---|
| 5,352,508 A | 10/1994 | Cheong |
| 6,051,747 A | 4/2000 | Lindqvist ................ 602/46 |
| 6,146,654 A | 11/2000 | Kubo |
| 6,180,133 B1 * | 1/2001 | Quan et al. .............. 424/448 |
| 6,207,875 B1 | 3/2001 | Lindqvist ................ 602/46 |
| 6,794,555 B2 | 9/2004 | Apert et al. .............. 602/48 |
| 8,263,100 B2 | 9/2012 | Areskoug et al. ......... 424/409 |
| 2003/0036717 A1 | 2/2003 | Apert et al. .............. 602/48 |
| 2005/0266081 A1 * | 12/2005 | Rogozinski .............. 424/484 |
| 2009/0047332 A1 * | 2/2009 | Kim et al. ............... 424/445 |
| 2010/0286584 A1 | 11/2010 | Areskoug et al. ......... 602/46 |
| 2011/0028919 A1 | 2/2011 | Johnnison et al. ......... 604/319 |

FOREIGN PATENT DOCUMENTS

| | | | |
|---|---|---|---|
| EP | 0475807 A2 | 3/1992 | |
| EP | 1274473 | 1/2003 | |
| JP | H03-167116 A | 7/1991 | |
| JP | H09-328418 A | 12/1997 | |
| KR | 100859339 B1 | 9/2008 | |
| SE | 1050367-0 | 4/2010 | |
| WO | WO 93/19710 | 10/1993 | |
| WO | WO-98/23305 A1 | 6/1998 | |
| WO | WO 01/80920 | 11/2001 | |
| WO | WO 02/36866 | 5/2002 | |
| WO | WO 02/062403 | 8/2002 | |
| WO | WO-2005/102403 A1 | 11/2005 | |
| WO | WO 2007/105883 | 9/2007 | |
| WO | WO 2008/057155 | * 5/2008 | ............ C09J 183/04 |
| WO | WO 2011/129759 | 10/2011 | |

OTHER PUBLICATIONS

U.S. Appl. No. 61/323,926, Lowenhielm, et al., filed Apr. 14, 2010.
International Preliminary Report on Patentability issued on Oct. 16, 2012 for International Patent Application No. PCT/SE2011/050452, which was filed on Apr. 13, 2011 [Inventor—Lowenhielm; Applicant—Mölnlycke Health Care AB] [6 pages].
Written Opinion issued on Aug. 11, 2011 for International Patent Application No. PCT/SE2011/050452, which was filed on Apr. 13, 2011 [Inventor—Lowenhielm; Applicant—Mölnlycke Health Care AB] [5 pages].
International Search Report issued on Aug. 10, 2011 for International Patent Application No. PCT/SE2011/050452, which was filed on Apr. 13, 2011 [Inventor—Lowenhielm; Applicant—Mölnlycke Health Care AB] [4 pages].
Issue Notification issued on Aug. 22, 2012 for U.S. Appl. No. 12/529,430, filed Mar. 19, 2010 [Inventor—Areskoug; Applicant—Mölnlycke Health Care AB] [1 page].
Notice of Allowance issued on Jun. 15, 2012 for U.S. Appl. No. 12/529,430, filed Mar. 19, 2010 [Inventor—Areskoug; Applicant—Mölnlycke Health Care AB] [6 pages].
Notice of Allowance issued on Jun. 11, 2012 for U.S. Appl. No. 12/529,430, filed Mar. 19, 2010 [Inventor—Areskoug; Applicant—Mölnlycke Health Care AB] [8 pages].
Examiner-Initiated Interview Summary issued on Jun. 1, 2012 for U.S. Appl. No. 12/529,430, filed Mar. 19, 2010 [Inventor—Areskoug; Applicant—Mölnlycke Health Care AB] [1 page].
Response to Restriction Requirement filed on Apr. 12, 2012 for U.S. Appl. No. 12/529,430, filed Mar. 19, 2010 [Inventor—Areskoug; Applicant—Mölnlycke Health Care AB] [7 pages].

(Continued)

*Primary Examiner* — Brian Gulledge
(74) *Attorney, Agent, or Firm* — Ballard Spahr LLP

(57) ABSTRACT

The present invention pertains to antimicrobial compositions comprising inter alia at least one alkenyl- and/or alkynyl-substituted polysiloxane, at least one polysiloxane comprising silicon-bonded hydrogen atoms, and at least one hydrosilylation catalyst, as well as antimicrobial silicone gels, wound dressings, and methods of preparing the above.

50 Claims, 4 Drawing Sheets

(56) References Cited

OTHER PUBLICATIONS

Restriction Requirement issued on Feb. 23, 2012 for U.S. Appl. No. 12/529,430, filed Mar. 19, 2010 [Inventor—Areskoug; Applicant—Mölnlycke Health Care AB] [6 pages].
Preliminary Amendment filed on Sep. 1, 2009 for U.S. Appl. No. 12/529,430, filed Mar. 19, 2010 [Inventor—Areskoug; Applicant—Mölnlycke Health Care AB] [8 pages].
PACER Listing of Docket Entries, 2010.
Stipulation of Dismissal; Sep. 16, 2008.
Deposition of Stephen J. Clarson, Ph.D.; Feb. 1, 2007.
Deposition of Stephen J. Clarson, Ph.D.; Mar. 6, 2008.
Markman Order; Jun. 21, 2007.
First Amended Complaint and Demand for Jury Trial; Jun. 15, 2006.
Preliminary Constructions of Defendants Medline Industries, Inc. and Ossur HF; Dec. 21, 2006.
Joint Claim Construction Statement; Jan. 16, 2007.
Exhibit A of Joint Claim Construction Statement—Parties' proposed constructions of each disputed claim term, phrase, or clause and support for such constructions; Jan. 16, 2007.
Exhibit B of Joint Claim Construction Statement—Summary of Opinions of Dr. Stephen J. Clarson; Jan. 16, 2007.
Claim Constructing Brief of Defendants Medline Industries, Inc. and Ossur HF; Feb. 7, 2007.
Mölnlycke Health Care AB and Mölnlycke Health Care US Opening Claim Construction Brief; Feb. 7, 2007.
Exhibit 1 of Mölnlycke Health Care AB and Mölnlycke Health Care US Opening Claim Construction Brief—U.S. Pat. No. 6,051,747; Feb. 7, 2007.
Exhibit 2, Parts A-I of Mölnlycke Health Care AB and Mölnlycke Health Care US Opening Claim Construction Brief—Gentleheal® Marketing Materials; Feb. 7, 2007.
Exhibit 3 of Mölnlycke Health Care AB and Mölnlycke Health Care US Opening Claim Construction Brief—Excerpts of Technical Dictionaries in the Chemical and Medical Fields; Feb. 7, 2007.
Exhibit 4 Parts A-E of Mölnlycke Health Care AB and Mölnlycke Health Care US Opening Claim Construction Brief—Excerpts of General purpose dictionaries; Feb. 7, 2007.
Exhibit 5 Parts A-B of Mölnlycke Health Care AB and Mölnlycke Health Care US Opening Claim Construction Brief—U.S. Pat. No. 7,154,017; Feb. 7, 2007.
Excerpts of Videotaped Deposition of Dr. Steven J. Clarson; Feb. 7, 2007.
Excerpts of Videotaped Deposition of Tomas T. Fabo; Feb. 7, 2007.
Responsive Claim Construction Brief of Defendants Medline Industries, Inc. and Ossur HF; Feb. 7, 2007.
Mölnlycke Health Care AB and Mölnlycke Health Care US Response to Medline Industries, Inc. and Ossur HF Opening Claim Construction Brief; Feb. 7, 2007.
Order; Jun. 21, 2007.
Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order; Nov. 5, 2007.
Exhibit A of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—U.S. Pat. No. 6,051,747; Nov. 5, 2007.
Exhibit B of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Defendants Medline Industries, Inc. and Ossur HF Disclosure of Invalidity Contentions; Nov. 5, 2007.
Exhibit C of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Jan. 31, 2007 Videotaped Deposition of Tomas T. Fabo; Nov. 5, 2007.
Exhibit D of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Aug. 21, 2007 Videotaped Deposition of Tomas T. Fabo; Nov. 5, 2007.
Exhibit E of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Correspondence dated Oct. 8, 2007 from Mr. Baldassare Vinti to Mr. Steve Moore; Nov. 5, 2007.
Exhibit F of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Jul. 25, 2007 Hearing; Nov. 5, 2007.
Exhibit G of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Defendants' Objections and Responses to Plaintiffs' First Set of Continuing Interrogatories; Nov. 5, 2007.
Exhibit H of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Sep. 6, 2007 Deposition of Jonathan Primer; Nov. 5, 2007.
Exhibit I of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Sep. 27, 2007 Deposition of Hilmar Jannusson; Nov. 5, 2007.
Exhibit J of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Plaintiffs' Objections to Notice of 30(b)(6) Depositions Concerning the Issues of Infringement, Validity, and Enforceability; Nov. 5, 2007.
Medline Industries, Inc. and Ossur HF Motion for Summary Judgment of Invalidity; Mar. 26, 2008.
Medline Industries, Inc. and Ossur HF Memorandum of Law in Support of Motion for Summary Judgment of Invalidity; Mar. 26, 2008.
Medline Industries, Inc. and Ossur HF Rule 56.1 Statement of Undisputed Material Facts; Mar. 26, 2008.
Declaration of Jennifer R. Scullion in Support of Medline Industries, Inc. and Ossur HF Motion for Summary Judgment of Invalidity; Mar. 26, 2008.
Exhibit A of Medline Industries, Inc. and Ossur HF Rule 56.1 Statement of Undisputed Material Facts—U.S. Pat. No. 6,051,747; Mar. 26, 2008.
Exhibit B of Medline Industries, Inc. and Ossur HF Rule 56.1 Statement of Undisputed Material Facts—U.S. Pat. No. 4,921,704; Mar. 26, 2008.
Exhibit C of Medline Industries, Inc. and Ossur HF Rule 56.1 Statement of Undisputed Material Facts—U.S. Pat. No. 5,340,363; Mar. 26, 2008.
Exhibit D of Medline Industries, Inc. and Ossur HF Rule 56.1 Statement of Undisputed Material Facts—EP Patent No. 0 261 167; Mar. 26, 2008.
Exhibit E of Medline Industries, Inc. and Ossur HF Rule 56.1 Statement of Undisputed Material Facts—U.S. Pat. No. 5,540,922; Mar. 26, 2008.
Exhibit F of Medline Industries, Inc. and Ossur HF Rule 56.1 Statement of Undisputed Material Facts—U.S. Pat. No. 5,635,201; Mar. 26, 2008.
Exhibit G of Medline Industries, Inc. and Ossur HF Rule 56.1 Statement of Undisputed Material Facts—British Patent No. 898,826; Mar. 26, 2008.
Exhibit H of Medline Industries, Inc. and Ossur HF Rule 56.1 Statement of Undisputed Material Facts—Excerpts of Jan. 31, 2007 Videotaped Deposition of Tomas T. Fabo; Mar. 26, 2008.
Exhibit I of Medline Industries, Inc. and Ossur HF Rule 56.1 Statement of Undisputed Material Facts—Excerpts of Aug. 21, 2007 Videotaped Deposition of Tomas T. Fabo; Mar. 26, 2008.

(56) References Cited

OTHER PUBLICATIONS

Exhibit J of Medline Industries, Inc. and Ossur HF Rule 56.1 Statement of Undisputed Material Facts—Excerpts of Videotaped Deposition of Dr. Steven J. Clarson; Mar. 26, 2008.
Exhibit K of Medline Industries, Inc. and Ossur HF Rule 56.1 Statement of Undisputed Material Facts—Excerpts of Videotaped Deposition of Craig Broussard, Ph.D., R.N; Mar. 26, 2008.
Exhibit L of Medline Industries, Inc. and Ossur HF Rule 56.1 Statement of Undisputed Material Facts—Excerpts of Videotaped Deposition of Larry Bogart; v, Mar. 26, 2008.
Exhibit M of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit N of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit O of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit P of Medline Industries, Inc. and Ossur HF Rule 56.1 Statement of Undisputed Material Facts—Excerpts of the Prosecution File of U.S. Pat. No. 6,051,747; Mar. 26, 2008.
Exhibit Q of Medline Industries, Inc. and Ossur HF Rule 56.1 Statement of Undisputed Material Facts—Initial Memorandum of the Fabo Interference Proceeding; Mar. 26, 2008.
Exhibit R of Medline Industries, Inc. and Ossur HF Rule 56.1 Statement of Undisputed Material Facts—Sua Sponte Holding of Unpatentability in View of Prior Art; Mar. 26, 2008.
Exhibit S of Medline Industries, Inc. and Ossur HF Rule 56.1 Statement of Undisputed Material Facts—Mölnlycke Health Care AB and Mölnlycke Health Care US Supplemental Answers to Defendant Ossur HF's First Set of Interrogatories; Mar. 26, 2008.
Exhibit T of Medline Industries, Inc. and Ossur HF Rule 56.1 Statement of Undisputed Material Facts—Mölnlycke Health Care AB and Mölnlycke Health Care US Response to Medline Industries, Inc. and Ossur HF Claim Construction Brief; Mar. 26, 2008.
Expert Declaration of Dr. Michael A. Brook in Support of Medline Industries, Inc. and Ossur HF Motion for Summary Judgment; Mar. 26, 2008.
Exhibit A of Expert Declaration of Dr. Michael A. Brook in Support of Medline Industries, Inc. and Ossur HF Motion for Summary Judgment—Curriculum Vitae; Mar. 26, 2008.
Exhibit B of Expert Declaration of Dr. Michael A. Brook in Support of Medline Industries, Inc. and Ossur HF Motion for Summary Judgment—Expert Report of Michael A. Brook, Ph. D. on Validity Issues; Mar. 26, 2008.
Mölnlycke Health Care AB and Mölnlycke Health Care US Motion for Partial Summary Judgment That U.S. Pat. No. 6,051,747 is Not Invalid; Mar. 26, 2008.
Placeholder for Brief in Support of Mölnlycke Health Care AB and Mölnlycke Health Care US Motion for Partial Summary Judgment That U.S. Pat. No. 6,051,747 is not Invalid Filed Under Seal Pursuant to Revised Protective Order Submitted to the Court on Sep. 21, 2007; Mar. 26, 2008.
Mölnlycke Health Care AB and Mölnlycke Health Care US Statement of Undisputed Material Facts in Support of Motion to Strike Medline Industries, Inc. and Ossur HF New and Untimely Noninfringing Alternative Theory, Including Exhibits 1-9 Filed Under Seal Pursuant to Revised Protective Order; Mar. 26, 2008.
Excerpts of Videotaped Deposition of Andrew Martin Reed, Ph.D.; Mar. 26, 2008.
Excerpts of Videotaped Deposition of Laura Shafer; Mar. 26, 2008.
Excerpts of Videotaped Deposition of Craig Broussard, Ph.D., R.N; Mar. 26, 2008.
Excerpts of Videotaped Deposition of Larry Bogart; Mar. 26, 2008.
Placeholder for Exhibit 6—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 7—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 8—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Excerpts of Jan. 31, 2007 Videotaped Deposition of Tomas T. Fabo; Mar. 26, 2008.
Placeholder for Exhibit 10—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 11—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 12—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 13—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 14—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 15—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 16—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Excerpts of Videotaped Deposition of James Wetrich; Mar. 26, 2008.
Placeholder for Exhibit 18—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 19—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Placeholder for Exhibit 20—Mölnlycke Health Care AB and Mölnlycke Health Care US Motion for Partial Summary Judgment That U.S. Pat. No. 6,051,747 is Not Invalid; Confidential—Filed Under Seal Pursuant to Revised Protective Order Submitted to the Court on Sep. 21, 2007; Mar. 26, 2008.
Excerpts of Deposition of Michael Brook; Mar. 26, 2008.
Mölnlycke Health Care AB and Mölnlycke Health Care US Brief in Opposition to Medline Industries, Inc. and Ossur HF Motion for Summary Judgment of Invalidity; Apr. 24, 2008.
Exhibit 23 of Mölnlycke Health Care AB and Mölnlycke Health Care US Brief in Opposition to Medline Industries, Inc. and Ossur HF Motion for Summary Judgment of Invalidity—Excerpts of videotaped deposition of Andrew Martin Reed, Ph. D.; Apr. 24, 2008.

(56) References Cited

OTHER PUBLICATIONS

Exhibit 24 of Mölnlycke Health Care AB and Molnlycke Health Care US Brief in Opposition to Medline Industries, Inc. and Ossur HF Motion for Summary Judgment of Invalidity—Excerpts of Deposition of Michael Brook; Apr. 24, 2008.
Exhibit 25 of Mölnlycke Health Care AB and Mölnlycke Health Care US Brief in Opposition to Medline Industries, Inc. and Ossur HF Motion for Summary Judgment of Invalidity—Excerpts of Videotaped Deposition of Dr. Steven J. Clarson; Apr. 24, 2008.
Exhibit 26 of Mölnlycke Health Care AB and Mölnlycke Health Care US Brief in Opposition to Medline Industries, Inc. and Ossur HF Motion for Summary Judgment of Invalidity—Excerpts of Videotaped Deposition of Larry Bogart; Apr. 24, 2008.
Exhibit 27 of Mölnlycke Health Care AB and Mölnlycke Health Care US Brief in Opposition to Medline Industries, Inc. and Ossur HF Motion for Summary Judgment of Invalidity—Excerpts of Deposition of Benoit Castel; Apr. 24, 2008.
Exhibit 28 of Mölnlycke Health Care AB and Mölnlycke Health Care US Brief in Opposition to Medline Industries, Inc. and Ossur HF Motion for Summary Judgment of Invalidity—*Ortho-McNeil Pharm., Inc* v. *Mylan Labs.,Inc.*, No. 2007-1223, 2008 WL 834402, at *5 (Fed. Cir. Mar. 31, 2008); Apr. 24, 2008.
Exhibit 29 of Mölnlycke Health Care AB and Mölnlycke Health Care US Brief in Opposition to Medline Industries, Inc. and Ossur HF Motion for Summary Judgment of Invalidity—Excerpts of Jan. 31, 2007 Videotaped Deposition of Tomas T. Fabo; Apr. 24, 2008.
Exhibit 30 of Mölnlycke Health Care AB and Mölnlycke Health Care US Brief in Opposition to Medline Industries, Inc. and Ossur HF Motion for Summary Judgment of Invalidity—Excerpts of Videotaped Deposition of Craig Broussard, Ph.D., R.N; Apr. 24, 2008.
Exhibit 31 of Mölnlycke Health Care AB and Mölnlycke Health Care US Brief in Opposition to Medline Industries, Inc. and Ossur HF Motion for Summary Judgment of Invalidity—Excerpts of the Prosecution File of U.S. Pat. No. 6,051,747; Apr. 24, 2008.
Declaration of Stephen J. Clarson, Ph.D.; Apr. 24, 2008.
Declaration of Tomas Fabo dated Apr. 24, 2008; Apr. 24, 2008.
Exhibit A of Declaration of Tomas Fabo—Sua Sponte Holding of Unpatentability in View of Prior Art; Apr. 24, 2008.
Exhibit B of Declaration of Tomas Fabo—Fabo Opposition to the Sua Sponte Holding of Unpatentability in View of Prior Art; Apr. 24, 2008.
Exhibit C of Declaration of Tomas Fabo—Declaration of Tomas Fabo dated Oct. 30, 1991; Apr. 24, 2008.
Exhibit D of Declaration of Tomas Fabo—Opinion on the Final Hearing before the Board of Patent Appeals and Interferences; Apr. 24, 2008.
Declaration of Larry Bogart; Apr. 24, 2008.
Exhibit A of Declaration of Larry Bogart—U.S. Pat. No. 5,856,245; Apr. 24, 2008.
Exhibit B of Declaration of Larry Bogart—U.S. Pat. No. 5,352,508; Apr. 24, 2008.
Medline Industries, Inc. and Ossur HF Memorandum of Law in Opposition to Mölnlycke's Motion for Partial Summary Judgment; Apr. 24, 2008.
1. Medline Industries, Inc. and Ossur HF Response to Mölnlycke Health Care AB and Mölnlycke Health Care US Statement of Undisputed Material Facts, and 2. Medline Industries, Inc. and Ossur HF Counter-Statement of Additional Material Facts; Apr. 24, 2008.
Declaration of Jennifer R. Scullion in Support of Medline Industries, Inc. and Ossur HF Opposition to Mölnlycke's Motion for Partial Summary Judgment; Apr. 24, 2008.
Exhibit U of Declaration of Jennifer R. Scullion in Support of Medline Industries, Inc. and Ossur HF Opposition to Mölnlycke's Motion for Partial Summary Judgment—U.S. Pat. No. 5,409,472; Apr. 24, 2008.
Exhibit V of Declaration of Jennifer R. Scullion in Support of Medline Industries, Inc. and Ossur HF Opposition to Mölnlycke's Motion for Partial Summary Judgment—U.S. Pat. No. 5,571,529; Apr. 24, 2008.
Exhibit W of Declaration of Jennifer R. Scullion in Support of Medline Industries, Inc. and Ossur HF Opposition to Mölnlycke's Motion for Partial Summary Judgment—UK Patent Application GB 2 290 031; Apr. 24, 2008.
Exhibit X of Declaration of Jennifer R. Scullion in Support of Medline Industries, Inc. and Ossur HF Opposition to Mölnlycke's Motion for Partial Summary Judgment—U.S. Pat. No. 3,972,328; Apr. 24, 2008.
Exhibit Y of Declaration of Jennifer R. Scullion in Support of Medline Industries, Inc. and Ossur HF Opposition to Mölnlycke's Motion for Partial Summary Judgment—U.S. Pat. No. 5,209,965; Apr. 24, 2008.
Exhibit Z of Declaration of Jennifer R. Scullion in Support of Medline Industries, Inc. and Ossur HF Opposition to Mölnlycke's Motion for Partial Summary Judgment—U.S. Pat. No. 5,445,604; Apr. 24, 2008.
Exhibit AA of Declaration of Jennifer R. Scullion in Support of Medline Industries, Inc. and Ossur HF Opposition to Mölnlycke's Motion for Partial Summary Judgment—U.S. Pat. No. 5,098,500; Apr. 24, 2008.
Exhibit BB of Declaration of Jennifer R. Scullion in Support of Medline Industries and Ossur HF Opposition to Mölnlycke's Motion for Partial Summary Judgment—U.S. Pat. No. 3,364,063; Apr. 24, 2008.
Exhibit CC of Declaration of Jennifer R. Scullion in Support of Medline Industries and Ossur HF Opposition to Mölnlycke's Motion for Partial Summary Judgment—U.S. Pat. No. 5,782,787; Apr. 24, 2008.
Exhibit DD of Declaration of Jennifer R. Scullion in Support of Medline Industries and Ossur HF Opposition to Mölnlycke's Motion for Partial Summary Judgment—U.S. Pat. No. 4,629,457; Apr. 24, 2008.
Exhibit EE of Declaration of Jennifer R. Scullion in Support of Medline Industries and Ossur HF Opposition to Mölnlycke's Motion for Partial Summary Judgment—U.S. Pat. No. 3,645,835; Apr. 24, 2008.
Exhibit FF of Declaration of Jennifer R. Scullion in Support of Medline Industries and Ossur HF Opposition to Mölnlycke's Motion for Partial Summary Judgment—U.S. Pat. No. 4,454,191; Apr. 24, 2008.
Exhibit GG of Declaration of Jennifer R. Scullion in Support of Medline Industries and Ossur HF Opposition to Mölnlycke's Motion for Partial Summary Judgment—U.S. Pat. No. 4,773,409; Apr. 24, 2008.
Exhibit HH of Declaration of Jennifer R. Scullion in Support of Medline Industries and Ossur HF Opposition to Mölnlycke's Motion for Partial Summary Judgment—Great Britain Patent No. 439,085; Apr. 24, 2008.
Exhibit II of Declaration of Jennifer R. Scullion in Support of Medline Industries and Ossur HF Opposition to Mölnlycke's Motion for Partial Summary Judgment—European Patent No. 0 230 387; Apr. 24, 2008.
Exhibit JJ of Declaration of Jennifer R. Scullion in Support of Medline Industries and Ossur HF Opposition to Mölnlycke's Motion for Partial Summary Judgment—U.S. Pat. No. 3,349,676; Apr. 24, 2008.
Exhibit KK of Declaration of Jennifer R. Scullion in Support of Medline Industries and Ossur HF Opposition to Mölnlycke's Motion for Partial Summary Judgment—U.S. Pat. No. 4,838,253; Apr. 24, 2008.
Exhibit LL of Declaration of Jennifer R. Scullion in Support of Medline Industries and Ossur HF Opposition to Mölnlycke's Motion for Partial Summary Judgment—US Patent Application 2004/0127839; Apr. 24, 2008.
Exhibit MM of Declaration of Jennifer R. Scullion in Support of Medline Industries and Ossur HF Opposition to Mölnlycke's Motion for Partial Summary Judgment—Excerpts from the Jan. 31, 2007 Videotaped Deposition of Tomas Fabo; Apr. 24, 2008.

(56) References Cited

OTHER PUBLICATIONS

Exhibit NN of Declaration of Jennifer R. Scullion in Support of Medline Industries and Ossur HF Opposition to Mölnlycke's Motion for Partial Summary Judgment—Excerpts from the Aug. 21, 2007 Video Deposition of Tomas Fabo; Apr. 24, 2008.
Exhibit OO of Declaration of Jennifer R. Scullion in Support of Medline Industries and Ossur HF Opposition to Mölnlycke's Motion for Partial Summary Judgment—Excerpts from the Videotaped Deposition of Steven Clarson; Apr. 24, 2008.
Exhibit PP of Declaration of Jennifer R. Scullion in Support of Medline Industries and Ossur HF Opposition to Mölnlycke's Motion for Partial Summary Judgment—Excerpts from the Videotaped Deposition of Craig Broussard; Apr. 24, 2008.
Exhibit QQ of Declaration of Jennifer R. Scullion in Support of Medline Industries and Ossur HF Opposition to Mölnlycke's Motion for Partial Summary Judgment—Excerpts from the Videotaped Deposition of Larry Bogart; Apr. 24, 2008.
Exhibit RR of Declaration of Jennifer R. Scullion in Support of Medline Industries and Ossur HF Opposition to Mölnlycke's Motion for Partial Summary Judgment—Excerpts from the Videotaped Deposition of Baldur Baldursson; Apr. 24, 2008.
Exhibit SS of Declaration of Jennifer R. Scullion in Support of Medline Industries and Ossur HF Opposition to Mölnlycke's Motion for Partial Summary Judgment—Excerpts from the Videotaped Deposition of Laura Shafer; Apr. 24, 2008.
Exhibit TT of Declaration of Jennifer R. Scullion in Support of Medline Industries and Ossur HF Opposition to Mölnlycke's Motion for Partial Summary Judgment—Excerpts from the Deposition of Hilmar Janusson; Apr. 24, 2008.
Exhibit VV of Declaration of Jennifer R. Scullion in Support of Medline Industries and Ossur HF Opposition to Mölnlycke's Motion for Partial Summary Judgment—Excerpts from the Oct. 8, 2007 deposition of Bengt Lindquist; Apr. 24, 2008.
Exhibit WW of Declaration of Jennifer R. Scullion in Support of Medline Industries and Ossur HF Opposition to Mölnlycke's Motion for Partial Summary Judgment—Excerpts from the Videotaped Deposition of Palmar Gudnason; Apr. 24, 2008.
Exhibit XX of Declaration of Jennifer R. Scullion in Support of Medline Industries and Ossur HF Opposition to Mölnlycke's Motion for Partial Summary Judgment—Excerpts from the Feb. 28, 2008 Deposition of Michael Brook; Apr. 24, 2008.
Exhibit YY of Declaration of Jennifer R. Scullion in Support of Medline Industries and Ossur HF Opposition to Mölnlycke's Motion for Partial Summary Judgment—Excerpts from the Videotaped Deposition of Andrew Martin Reed, Ph. D.; Apr. 24, 2008.
Exhibit ZZ of Declaration of Jennifer R. Scullion in Support of Medline Industries and Ossur HF Opposition to Mölnlycke's Motion for Partial Summary Judgment—Excerpts from the Video Deposition of Staffan Kuuse; Apr. 24, 2008.
Exhibit CCC of Declaration of Jennifer R. Scullion in Support of Medline Industries and Ossur HF Opposition to Mölnlycke's Motion for Partial Summary Judgment—Wound Care Project overview Exhibit No. 78; Apr. 24, 2008.
Exhibit DDD of Declaration of Jennifer R. Scullion in Support of Medline Industries and Ossur HF Opposition to Mölnlycke's Motion for Partial Summary Judgment—Medline's Production No. MED 001810 through 001816; Exhibit No. 20; Apr. 24, 2008.
Exhibit LLL of Declaration of Jennifer R. Scullion in Support of Medline Industries and Ossur HF Opposition to Mölnlycke's Motion for Partial Summary Judgment—Ossur's Production No. OS 046840 through 046851; Ulman et al., "Silicone Pressure Sensitive Adhesives for Healthcare Applications."; Apr. 24, 2008.
Exhibit MMM of Declaration of Jennifer R. Scullion in Support of Medline Industries and Ossur HF Opposition to Mölnlycke's Motion for Partial Summary Judgment—Excerpt from the file for Patent Interference Proceeding No. 102,565; Apr. 24, 2008.
Exhibit NNN of Declaration of Jennifer R. Scullion in Support of Medline Industries and Ossur HF Opposition to Mölnlycke's Motion for Partial Summary Judgment—Staffan Areskoug's Deposition Exhibit No. 6; "Design Input AiO-Dressing"; Apr. 24, 2008.

Expert Declaration of Dr. Michael A. Brook in Support of Medline Industries and Ossur HF Opposition to Mölnlycke Health Care AB and Mölnlycke Health Care US Motion for Partial Summary Judgment ; Apr. 24, 2008.
Exhibit C of Expert Declaration of Dr. Michael A. Brook in Support of Medline Industries and Ossur HF Opposition to Mölnlycke Health Care AB and Mölnlycke Health Care US Motion for Partial Summary Judgment—Expert Report of Michael A. Brook, Ph. D. on Validity Issues; Apr. 24, 2008.
Declaration of Andrew M. Reed, Ph.D. in Support of Medline Industries and Ossur HF Opposition to Mölnlycke Health Care AB and Mölnlycke Health Care US Motion for Partial Summary Judgment; Apr. 24, 2008.
Exhibit A of Declaration of Andrew M. Reed, Ph.D. in Support of Medline Industries and Ossur HF Opposition to Mölnlycke Health Care AB and Mölnlycke Health Care US Motion for Partial Summary Judgment—Curriculum Vitae of Andrew M. Reed; Apr. 24, 2008.
Exhibit B of Declaration of Andrew M. Reed, Ph.D. in Support of Medline Industries and Ossur HF Opposition to Mölnlycke Health Care AB and Mölnlycke Health Care US Motion for Partial Summary Judgment—Expert Report of Andrew M. Reed, Ph. D.; Apr. 24, 2008.
Mölnlycke Health Care AB and Mölnlycke Health Care US Reply Brief to Medline Industries and Ossur HF Opposition to Motion for Partial Summary Judgment that U.S. Pat. No. 6,051,747 is not Invalid; May 23, 2008.
Excerpts of Feb. 1, 2007 Videotaped Deposition of Dr. Steven J. Clarson; May 23, 2008.
Excerpts of Videotaped Deposition of Stefan Areskoug; May 23, 2008.
Excerpts of Mar. 6, 2008 Videotaped Deposition of Dr. Steven J. Clarson (Taken by Medline Industries and Ossur HF); May 23, 2008.
Excerpts of Aug. 21, 2007 Video Deposition of: Mr Tomas Fabo; May 23, 2008.
Exhibit 36 of Mölnlycke Health Care AB and Mölnlycke Health Care US Reply Brief to Medline Industries and Ossur HF Opposition to Motion for Partial Summary Judgment that U.S. Pat. No. 6,051,747 is Not Invalid; Filed Under Seal Pursuant to Protective Order; May 23, 2008.
Excerpts of Videotaped Deposition of James Wetrich; May 23, 2008.
Excerpts of Videotaped Deposition of Laura Shafer; May 23, 2008.
Excerpts of Videotaped Deposition of Craig Broussard, Ph.D., R.N.; May 23, 2008.
Excerpts of Videotaped Deposition of Larry Bogart; May 23, 2008.
Excerpts of Video Deposition of Staffan Kuuse; May 23, 2008.
Exhibit 42 of Mölnlycke Health Care AB and Mölnlycke Health Care US Reply Brief to Medline Industries and Ossur HF Opposition to Motion for Partial Summary Judgment that U.S. Pat. No. 6,051,747 is Not Invalid; Filed Under Seal Pursuant to Protective Order; May 23, 2008.
Excerpts of Video Deposition of Elisabet Lundqvist; May 23, 2008.
Second Declaration of Larry Bogart; May 23, 2008.
Expert Report of Mr. Larry Bogart dated Dec. 28, 2007; May 23, 2008.
Medline Industries and Ossur HF Reply Memorandum in Support of Motion for Summary Judgment of Invalidity; May 23, 2008.
Appendix of Unreported Authorities; May 23, 2008.
Excerpts from Manual of Patent Examining Procedure (Jul. 1997 Revisions); May 23, 2008.
Transcript of Videotaped Deposition of Tomas T. Fabo on Jan. 31, 2007 (215 pages); Jan. 31, 2007.
Transcript of Videotaped Deposition of James Wetrich (199 pages); Jan. 31, 2007.
Thomas X. "Silicone adhesives in healthcare applications." Dow Corning Health Care Industry, 2003.
Translation of Korean Patent No. 10-0859339, published on Sep. 22, 2008 (34 pages).

* cited by examiner

ANTIMICROBIAL GELS

CROSS-REFERENCE TO RELATED APPLICATIONS

The present application is a U.S. National Phase Application of International Application No. PCT/SE2011/050452, filed Apr. 13, 2011, which claims priority to Swedish Patent Application No. 1050367-0, filed Apr. 14, 2010, and U.S. Patent Application No. 61/323,926, filed Apr. 14, 2010, all of which applications are incorporated herein fully by this reference.

TECHNICAL FIELD

The present invention pertains to antimicrobial gel-forming compositions, antimicrobial silicone gels, and antimicrobial wound dressings comprising the antimicrobial silicone gels, as well as methods of preparing the above.

TECHNICAL BACKGROUND

The increasing prevalence of microbial strains exhibiting multidrug resistance as well as the surging pressure on healthcare systems worldwide have resulted in a veritable escalation over recent decades of nosocomial as well as community-acquired infections. Patients undergoing major surgical procedures, implantation of or interaction with medical devices, or patients with severe burns or chronic wounds, are particularly susceptible to microbial, notably bacterial and fungal, infections. Methicillin-resistant *Staphylococcus aureus*, *Pseudomonas aeruginosa*, as well as various yeast species of the genus *Candida*, are commonly associated with infected wounds and burns, often resulting in severe and complicated infections, placing additional burden on the healthcare system and on an already distressed patient.

Hygiene measures applied in healthcare settings, such as isolation of infected patients, improved surface sanitation, and the use of alcohol rubs and gels, undoubtedly mitigate the above problems to a certain extent, but adequate and efficacious wound care is a paramount determinant for preventing initial microbial colonization and subsequent spread of infectious diseases. Conventional wound dressings have long proved insufficient for treating, inter alia, severe burns and chronic wounds, with the implication that various types of antimicrobial dressings have been developed, comprising inter alia conventional antiseptics, antibiotics, antimicrobial peptides, or metallic agents with antimicrobial properties.

EP1274473, for instance, discloses antimicrobial coatings for wound dressings comprising a bioadsorbable substrate associated with one or more antimicrobial metals that releases said antimicrobial agent upon contact with an alcohol or water-based electrolyte. The bioadsorbable polymer is selected from a group comprising inter alia polyglycolic acid, glycolide, lactic acid, lactide, proteins, or polysaccharides.

The inherent antimicrobial properties of certain silver-containing compounds are being explored in various types of wound dressings. WO2002062403, inter alia, teaches a medical dressing comprising a complex of silver and being capable of releasing antimicrobial silver ion activity. More specifically, the silver complex comprises a combination of silver and a Group IV transition element, preferably zirconium, in order to enable controlled release of the silver ion to a wound bed.

US20030036717 describes an elastic compress consisting of an elastomeric matrix highly plasticized with a non-polar oil and containing a dispersed hydrocolloid. The compress additionally comprises at least one antiseptic agent, for instance a silver salt, and at least one surfactant for improving the bioavailability of the antiseptic agent.

Silicones are commonly utilized in various types of medical devices and in particular in wound dressings, as a result of its favourable intrinsic properties. Unlike many other materials used in wound dressings and medical devices, silicones possess attractive characteristics pertaining to inter alia manufacturing advantages, cohesion, tack, and adhesion, implying that they often constitute the materials of choice for wound dressing applications. WO1993019710 discloses an absorbent wound dressing comprising a layer of hydrophobic silicone gel, a layer of carrier material, and an absorbent body, providing a soft wound dressing having favourable properties relating to adhesive strength, ease of removal, and leakage prevention.

WO2008057155 discloses silicone gel forming compositions for temporarily adhering a medical device to a biological substrate, such as skin. Said disclosure teaches silicone gel compositions comprising active agents, for instance antibiotics, antiseptics, antifungals, anti-inflammatory agents, hormones, anticancer agents, histamine blockers, beta blockers, vitamins, sedatives, analgesics, proteolytic enzymes, and peptides, which can be bound in the composition. Further, WO2008057155 incidentally teaches including silver and derivatives as active agents that can be bound in the composition, but information about the parameters governing therapeutic efficacy, as well as efficacy validation, is largely absent.

SUMMARY OF THE INVENTION

It is hence an object of the present invention to overcome the above-identified problems and satisfy the existing needs within the art, i. e. to provide for facile and efficient manufacture of antimicrobial silicone-based compositions, gels, and wound dressings, as well as compositions, gels, and wound dressings per se having antimicrobial properties for adequate and efficacious wound treatment, through release of antimicrobial silver-containing compounds, in particular silver salts and/or silver ions. Thus, the present invention pertains to antimicrobial compositions, antimicrobial gels, and antimicrobial dressings, as well as methods for the preparation of said antimicrobial gels and dressings, and various uses thereof.

More specifically, the present invention relates to antimicrobial compositions comprising at least one alkenyl- and/or alkynyl-substituted polydiorganosiloxane, at least one polysiloxane comprising silicon-bonded hydrogen atoms and at least one hydrosilylation catalyst, wherein said composition further comprises at least one silver salt and at least one hydrophilic component (which may enhance silver release) that exerts a swelling effect, as well as antimicrobial gels produced from said antimicrobial composition through crosslinking the at least one alkenyl- and/or alkynyl-substituted polysiloxane and the at least one polysiloxane comprising silicon-bonded hydrogen atoms (i.e. Si—H moieties). Additionally, the invention pertains to further aspects relating to antimicrobial gels, inter alia prepared from compositions in accordance with the present invention, for instance through curing, as well as antimicrobial dressings comprising said antimicrobial gels. The antimicrobial gels as per the present invention may be formed by creating at least one covalent bond between at least one alkenyl and/or alkynyl moiety of a first polysiloxane and at least one Si—H moiety of second polysiloxane, said antimicrobial gel further comprising at least one hydrosilylation catalyst, wherein said antimicrobial gel further comprises at least one silver salt, and at least one (optionally silver release-enhancing) hydrophilic component that makes said antimicrobial gel swell at least 5% (wt/wt) after 24 hours in Solution A, as measured by the free swell absorption method.

Moreover, further aspects of the present invention pertain to methods of preparing said antimicrobial gels and dressing, comprising inter alia the steps of preparation of three mixtures, either simultaneously or sequentially or in any combinations of preparations. Said three mixtures may comprise (i) at least one alkenyl- and/or alkynyl-functional polysiloxane, at least one hydrosilylation catalyst and, optionally, silica particles, (ii) at least one alkenyl- and/or alkynyl-functional polysiloxane, at least one CE and/or at least one CL, and, optionally, silica particles, and (iii) at least one silver salt and at least one siloxane-containing copolymer. Subsequently, at least one silver-release enhancing hydrophilic component is mixed with mixture (i) and/or mixture (ii), followed by optionally heating the obtained mixture(s) to which the silver-release enhancing hydrophilic component was added, in order to melt the silver-release enhancing hydrophilic component. The resulting mixtures are thereafter mixed and, after optional coating of a suitable substrate, cured, thus creating either an antimicrobial gel and/or an antimicrobial dressing, in accordance with the present invention.

The present invention thus provides antimicrobial compositions, gels, and dressings having substantially improved properties compared to the antimicrobial products for wound treatment constituting the current art. The presence of silver-containing compounds, such as silver salts and/or silver ions, and (optionally silver release-enhancing) hydrophilic components in the compositions, as well as in the gels and dressings, confer antimicrobial properties not only to the products per se, but also imply that the silver salts/ions can exert antimicrobial effects in surrounding areas.

Further, the silver release can be modulated through the use of various different hydrophilic components that causes the compositions and gels to swell, thereby enhancing the inflow of liquid and the dispersions and distribution of the silver compounds, implying that the antimicrobial products and their intrinsic effects can be adapted to suit specific therapeutic purposes, for instance adjustment of the antimicrobial effects depending on the type and nature of wound/burn/injury to be treated, or depending on the infectious agent in question. Additionally, as an implication of the optimized physical and chemical properties resulting from the presence of various types of additives and excipients, inter alia siloxane-containing copolymers, silica particles, and siloxane polymer networks, the patient compliance and comfort, and consequently the antimicrobial efficacy, is optimized.

DETAILED DESCRIPTION OF THE INVENTION

Figure 1:
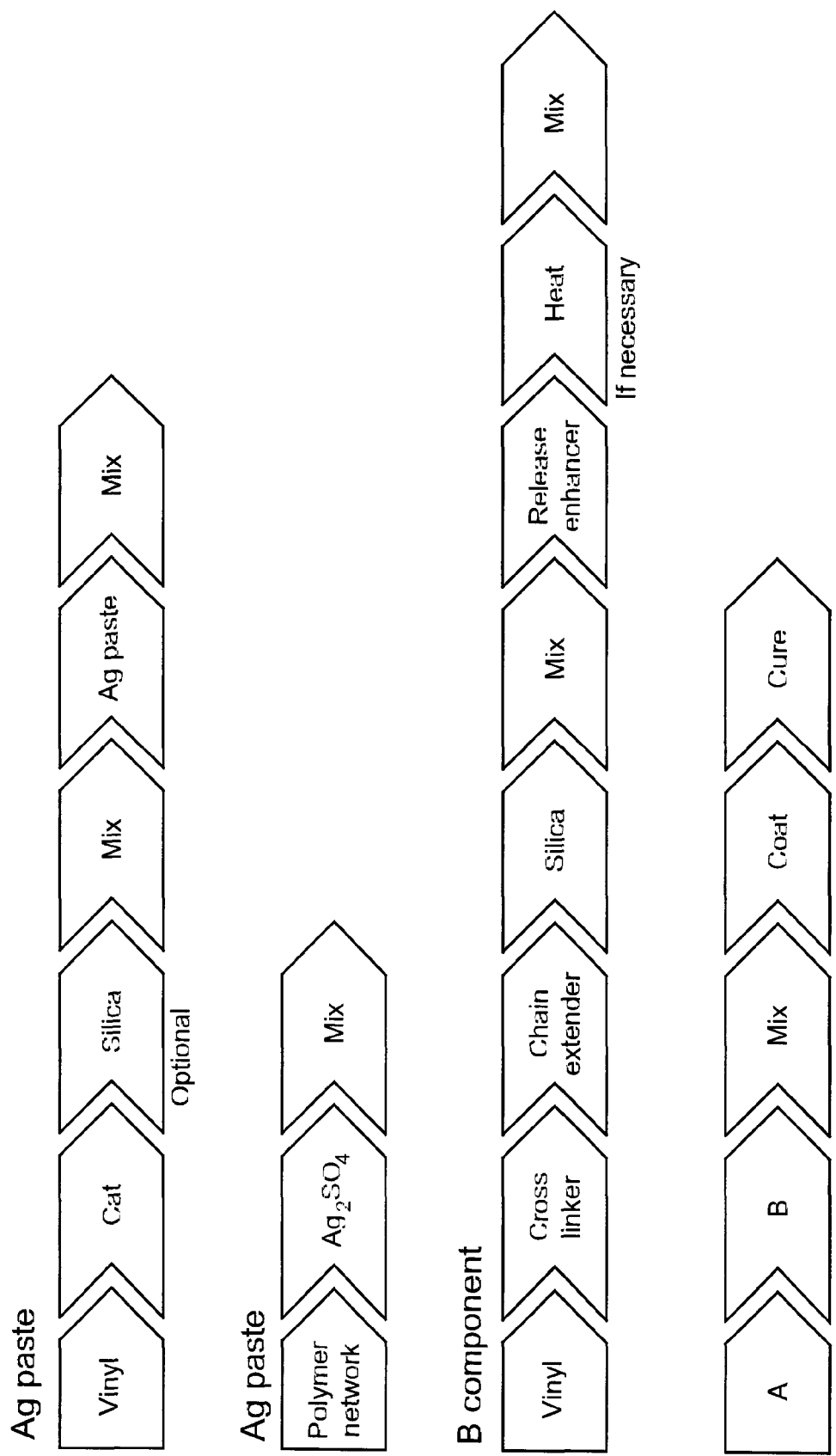
FIG. 1 portrays a flow chart describing the various steps associated with an exemplary manufacturing method for antimicrobial gels and/or dressings.
Figure 2:
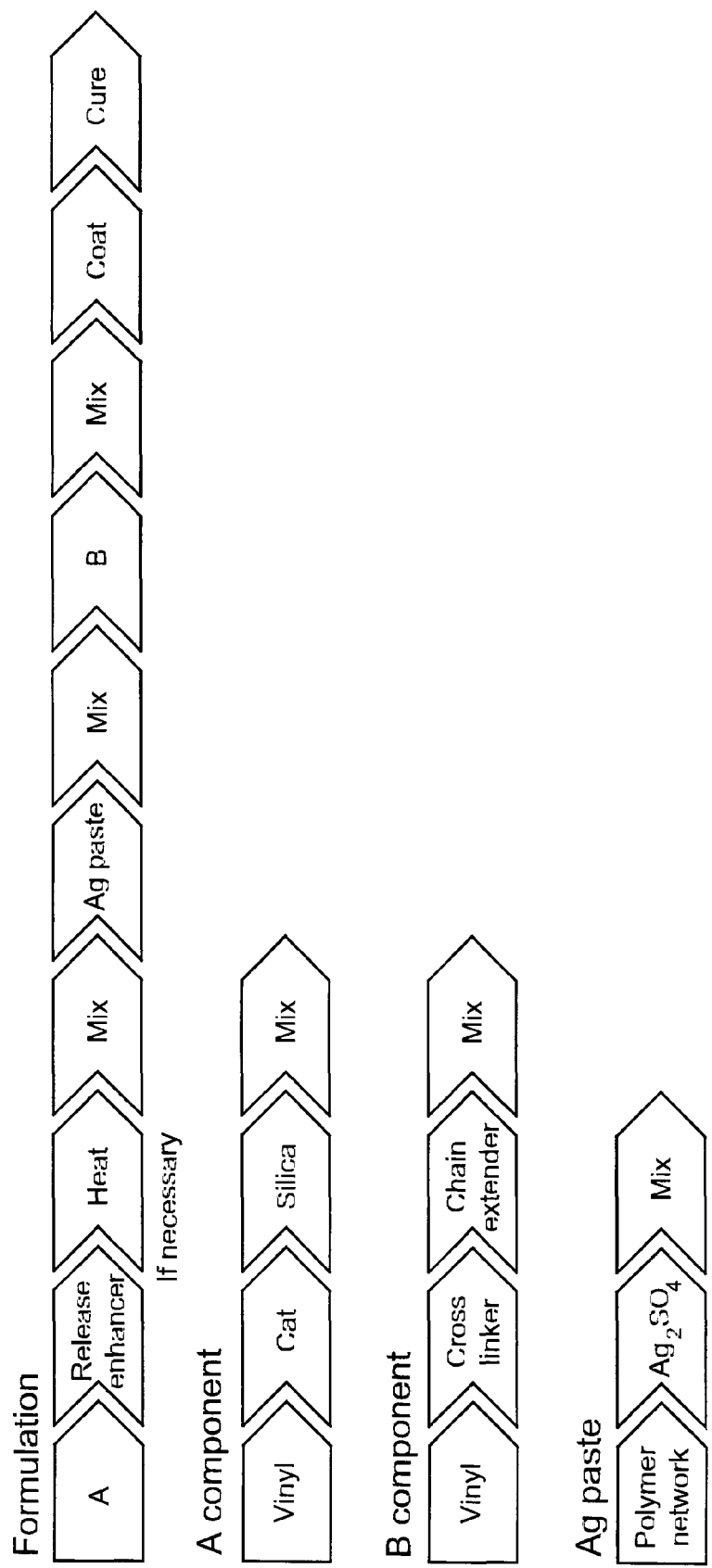
FIG. 2 illustrates a flow chart describing the various steps associated with an exemplary laboratory-scale preparation method for antimicrobial gels and dressings.

The present invention pertains inter alia to antimicrobial compositions that inhibit microbial growth, antimicrobial gels, produced inter alia from said compositions, various types of dressings comprising the antimicrobial gels for inhibiting microbial growth, as well as the use of the antimicrobial gels in various types of products for treating wounds and inhibiting microbial growth.

Where features, embodiments, or aspects of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in connection with one of the aspects and/or embodiments of the present invention also apply mutatis mutandis to all the other aspects and/or embodiments of the invention. For example, the at least one hydrophilic component (which may enhance silver release) described in connection with the antimicrobial compositions may naturally also be included in the antimicrobial gels, the excipients described in connection with the antimicrobial gels may also be comprised in the antimicrobial compositions, the at least one silver salt as well as the concentration of the at least one silver salt described in connection with the antimicrobial compositions naturally also apply to the antimicrobial gels, and the antimicrobial effects described in connection with a certain aspect and/or embodiment relating to a certain antimicrobial gel may also be exerted by other antimicrobial gels, all in accordance with the present invention.

A first aspect of the present invention relates to antimicrobial, silicone gel-forming compositions inhibiting microbial growth, wherein the compositions comprise at least one alkenyl- and/or alkynyl-substituted polysiloxane, at least one polysiloxane comprising silicon-bonded hydrogen atoms, and at least one hydrosilylation catalyst, wherein said composition further comprises at least one silver salt and at least one (optionally silver release-enhancing) hydrophilic component, and wherein said at least one hydrophilic component makes said antimicrobial composition, when cross-linked, swell at least 5% (wt/wt) after 24 hours in Solution A, as measured by the free swell absorption method. In further embodiments as per the present invention, the swelling may be at least 10% (wt/wt) after 24 hours in Solution A, or at least 20% (wt/wt) after 24 hours in Solution A, or at least 20% (wt/wt) after 24 hours in Solution A, or at least 30% (wt/wt) after 24 hours in Solution A, or at least 40% (wt/wt) after 24 hours in Solution A, or at least 50% (wt/wt) after 24 hours in Solution A, or at least 75% (wt/wt) after 24 hours in Solution A, or at least 100% (wt/wt) after 24 hours in Solution A, or at least 150% (wt/wt) after 24 hours in Solution A, or at least 200% (wt/wt) after 24 hours in Solution A, or at least 300% (wt/wt) after 24 hours in Solution A, or at least 400% (wt/wt) after 24 hours in Solution A, or at least 500% (wt/wt) after 24 hours in Solution A, or at least 600% (wt/wt) after 24 hours in Solution A, or at least 700% (wt/wt) after 24 hours in Solution A or at least 800% (wt/wt) after 24 hours in Solution A or any other lower or higher value, and any interval created by the above figures e.g. from 5% (wt/wt) to 800% (wt/wt) after 24 hours in Solution A.

Optionally, the swelling may be measured at different time points, for instance at 48 hours or at 72 hours, and also at these time points the swelling may be at least 10% (wt/wt) after 24 hours in Solution A, or at least 20% (wt/wt) after 24 hours in Solution A, or at least 20% (wt/wt) after 24 hours in Solution A, or at least 30% (wt/wt) after 24 hours in Solution A, or at least 40% (wt/wt) after 24 hours in Solution A, or at least 50% (wt/wt) after 24 hours in Solution A, or at least 75% (wt/wt) after 24 hours in Solution A, or at least 100% (wt/wt) after 24 hours in Solution A, or at least 150% (wt/wt) after 24 hours in Solution A, or at least 200% (wt/wt) after 24 hours in Solution A, or at least 300% (wt/wt) after 24 hours in Solution A, or at least 400% (wt/wt) after 24 hours in Solution A, or at least 500% (wt/wt) after 24 hours in Solution A, or at least 600% (wt/wt) after 24 hours in Solution A, or at least 700% (wt/wt) after 24 hours in Solution A or at least 800% (wt/wt) after 24 hours in Solution A or any other lower or higher value, and any interval created by the above figures e.g. from 5% (wt/wt) to 800% (wt/wt) after 24 hours in Solution A.

The free swell absorption method employing Solution A is a standard methodology used within the field for assessing swelling capacity. The free swell method is described in more detail below, but briefly the assay encompasses placing a pre-weighed dressing sample in a quantity of test solution (in this case, Solution A) which is 40 times the mass of the sample. The sample is then allowed to absorb Solution A for a specific time at a specific temperature, after which the sample is weighed again, in order to determine the free swell absorption capacity.

The silver compounds and/or salts endow the composition with antimicrobial properties, whereas the release-enhancing hydrophilic component promotes efficient release of the silver salt, thereby enhancing the antimicrobial efficacy of the composition. Without wishing to be bound by any particular theory, it is surmised that the presence of at least one hydrophilic component exhibiting a certain free swell in the antimicrobial composition increases the solubilization, the dispersion, and the inflow of liquid into the composition, thereby increasing the release of silver and increasing the antimicrobial properties of the composition.

The at least one polysiloxane comprising silicon-bonded hydrogen atoms may, as is well-known within the art, comprise inter alia at least one chain extender (CE) and/or at least one crosslinker (CL). Chain extenders generally comprise polysiloxanes having hydrogen atoms attached to terminal silicon-atoms, whereas crosslinkers normally comprise polysiloxanes having hydrogen-substituted silicon atoms covalently bound only to the internal, non-terminal silicon atoms. Both branched and linear polysiloxanes having various different chemical natures as well as various viscosities may be utilized in accordance with the present invention. The at least one alkenyl- and/or alkynyl-substituted polydiorganosiloxane and the at least one polysiloxane comprising silicon-bonded hydrogen atoms may have hydrogen or various hydrocarbon substituents, such as saturated or unsaturated, branched or linear, $C_1$-$C_{20}$, preferably $C_1$-$C_5$, hydrocarbon chains, optionally with heteroatoms present. In accordance with the aspects and embodiments of the present invention, said organic substituents may comprise methyl, ethyl, propyl, butyl, vinyl, allyl, and/or aryl, and combinations of these, in any suitable position, for instance as pendant or terminal groups. The term "alkenyl- and/or alkynyl-substituted polysiloxane" is to be understood as comprising polydiorganosiloxanes substituted with groups comprising unsaturated carbon-carbon bonds, i.e. both carbon-carbon double bonds and/or carbon-carbon triple bonds. Thus, the term "alkenyl- and/or alkynyl-substituted polysiloxane" shall be understood as comprising both alkenyl-substituted polysiloxanes as well as alkynyl-substituted polysiloxanes, as well as alkenyl and alkynyl-substituted polysiloxanes. Further, the term "when cross-linked" shall be understood to relate to the cross-link that can be created between alkenyl and/alkynyl moieties (i.e. unsaturations) of at least one polysiloxane and the Si—H moiety of a second polysiloxane. Additionally, the term "polysiloxane" shall be understood to pertain to all types of polysiloxanes, for instance polydiorganosiloxanes, etc., and within the context of the present invention, these two terms are used interchangeably. Finally, the process feature of "mixing mixture (i) and mixture (ii)" shall be understood to relate to mixing the mixture remaining after the preceding method step (i.e. the mixture that was not mixed with mixture (iii)) with the mixture obtained in the previous step (i.e. with mixture (iii) combined with either mixture (i) and/or mixture (ii)).

Further in accordance with the aspects and embodiments of the present invention, it is important that moieties capable of crosslinking the at least one alkenyl- and/or alkynyl-substituted polysiloxane and the at least one polysiloxane comprising silicon-bonded hydrogen atoms (i.e. an Si—H moiety), upon reacting said components, are present, in order to mediate formation of silicone gels. Mechanisms within the present invention for reacting, and thereby cross-linking, the at least one alkenyl- and/or alkynyl-substituted polysiloxane and the at least one polysiloxane comprising silicon-bonded hydrogen atoms comprises hydrosilylation, in which a polysiloxane having an Si—H reactive group reacts with a polysiloxane (polydiorganosiloxane) having an aliphatically unsaturated reactive group, in the presence of a hydrosilylation catalyst, typically Pt and/or Pd. Typical silicone gel forming compositions include alkenyl- and/or alkynyl-functional polyorganosiloxanes (e.g. vinyl functional polyorganosiloxanes), α,ω-hydrogen polyorganosiloxanes, i. e. chain extenders, hydrogen-functional polyorganosiloxanes, i. e. cross-linkers, and a hydrosilylation catalyst (e.g. a platinum complex).

Further in line with the present invention, the viscosities of the at least one alkenyl- and/or alkynyl-substituted polydiorganosiloxane and the at least one polysiloxane comprising silicon-bonded hydrogen atoms may vary in accordance with the desired properties of the resultant antimicrobial gels and dressings, in accordance with the aspects and the embodiments of the invention. As per an embodiment of the present invention, a mixture of the at least one alkenyl- and/or alkynyl-substituted polydiorganosiloxane and the at least one polysiloxane comprising silicon-bonded hydrogen atoms may have a viscosity at ambient temperature and 1 atmosphere between 500 and 100,000 cSt, preferably between 500 and 20,000 cSt, prior to the addition of any additives and/or excipients, and before cross-linking of the at least one alkenyl- and/or alkynyl-substituted polydiorganosiloxane and the at least one polysiloxane comprising silicon-bonded hydrogen atoms.

In one embodiment of the present invention, the at least one (optionally silver release-enhancing) hydrophilic component may inter alia be selected from the group comprising mono- di- and/or polysaccharides, sugar alcohols, polyols, polyethers, polyesters, polyamides and/or polymers comprising pendant carboxylic acid groups and/or pendant sulphonate groups, but other hydrophilic polymers and molecules are also within the scope of the invention. In a further embodiment, the at least one hydrophilic component may for instance be selected from the group comprising glucose, xylitol, sorbitol, mannitol, cyclodextrins, cellulose, hemicellulose, carboxymethylated cellulose, chitosan, dextran, chitin, amylose, amylopectin, polyethylene glycol, polypropylene glycol, copolymers of polyethylene glycol and polypropylene glycol, polyglycerol, poly(acrylic acid), copolymers of acrylic acid and $C_{10}$-$C_{30}$ alkyl acrylate, poly(acrylamide), maleic anhydride polymers and copolymers, carboxy methyl cellulose, methyl cellulose, hydroxymethylpropylcellulose, ethylcellulose, carboxyethylcellulose, hydroxypropylcellulose, hydroxyethylcellulose, carboxymethylcellulose, cellulose alkyl sulfonate, polystyrene sulphonates, vinyl acids and vinyl alcohols. In yet another embodiment, the hydrophilic component is preferably present in a concentration that ranges from approximately 3% to 40% (w/w), and more preferably from 4% to 30%.

In a further embodiment, numerous different types of silver salts with antimicrobial properties are within scope of the present invention, and the at least one silver salt may thus for instance be selected from the group comprising $Ag_2SO_4$, $Ag_2SO_3$, $AgNO_3$, $Ag_2CO_3$, $Ag_3PO_4$, silver zirconium, and/or organic silver salts, such as silver citrate, silver acetate, silver lactate and/or combinations or mixtures thereof. Various other compounds providing silver ions are conceivable and such compounds are also within the spirit of the present invention. In an embodiment of the present invention, the silver salt concentration may range from approximately 1% to 30%, and preferably from approximately 2% to 20%. As the silver salt is the primary antimicrobial agent bestowing the composition with its antimicrobial properties, it is conceivable that an increasing silver concentration would correspond to an improved overall antimicrobial effect. However, without wishing to be bound by any particular theory, it is surmised that it may potentially also be essential to provide compositions and gels with optimized combinations of silver release properties and silver salt concentration, as illustrated by the efficacy of the antimicrobial compositions and gels of the present invention. Nevertheless, other aspects and embodiment of the present invention may also contribute the antimicrobial properties.

In order to further improve the antimicrobial and overall properties of the antimicrobial composition, further embodiments of the present invention relate to compositions that may comprise at least one siloxane-containing copolymer selected from the group comprising at least one siloxane polymer network and at least one siloxane polyether (SPE). The at least one siloxane polymer network may comprise for instance at least one cross-polymer and/or at least one ter-polymer. SPEs are block copolymers with segments comprising polysiloxane (for instance PDMS) and additional segments containing at least one type of polyether, for instance polyethyleneglycol (PEG) or polypropylenglycol (PPG). Suitable SPEs may for instance be selected from the group comprising bis-isobutyl PEG/PPG-10/7 dimethicone copolymer (Dow Corning Toray FZ 2233) and Silwet 8500 (from Momentive).

In yet another embodiment, the siloxane polymer network may for instance be present at a concentration of between approximately 2% and 30%, preferably between 5% and 20%, and it may, in accordance with an additional embodiment, for instance be selected from the group comprising poly-ether-siloxane copolymer networks, cyclopentasiloxane-alkyl cetearyl dimethicone copolymer networks (Velvesil 125), and vinyldimethyl/trimethylsiloxysilicate stearyl dimethicone crosspolymer.

Polydimethylsiloxane (PDMS) copolymers, i.e. suitable siloxane-containing polymers in accordance with the present invention, consist of at least two different polymer types, which are arranged in blocks of PDMS and the other polymer, for example polyethylene oxide. When three different polymer components are present in the same polymer, it is termed a terpolymer. Common architectures of copolymers are linear, where the at least two different blocks are arranged in series, or graft copolymers, where for example PEO is grafted along a PDMS backbone, resembling a comb. The relative abundance of the PDMS and the other polymer components will determine properties such as hydrophilicity, which is one of the desirable properties as per the present invention. The co- and terpolymers may also be intramolecularly crosslinked, in which case the polymers form a network (sometimes termed crosspolymer). Said network may be swollen in solvents, for example cyclic siloxanes to form a gel, with advantages relating to for instance ease of processing, in spite of the crosslinked polymer itself having very high viscosity.

In further embodiments of the present invention, the antimicrobial compositions and gels may comprise particles for facilitating and/or enabling the dispersion of constituents of the composition, primarily certain silver-release enhancing hydrophilic components but potentially also the antimicrobial silver salts. As per an embodiment of the present invention, particles conceivable within the scope of the invention may for instance be silica particles, but other suitable particles are also within the scope of the present invention. The particles may be present in a concentration ranging from 2 to 5%, preferably between 2 to 3%. In accordance with another embodiment of the present invention, the antimicrobial composition may further comprise at least one siloxane-containing copolymer. Said siloxane-containing copolymer may for instance comprise a hydrophilic polymer, such as PEG or PPG, or other polymers known to a person skilled in the art.

In yet other embodiments of the antimicrobial compositions of the present invention, the at least one alkenyl- and/or alkynyl-substituted polydiorganosiloxane may be covalently crosslinked to the at least one polysiloxane comprising silicon-bonded hydrogen atoms, thereby forming an antimicrobial gel.

A second aspect of the present invention pertains to antimicrobial gels comprising at least one alkenyl- and/or alkynyl-substituted polysiloxane (polydiorganosiloxanes) covalently bound to at least one polysiloxane comprising silicon-bonded hydrogen atoms, said antimicrobial gel further comprising at least one hydrosilylation catalyst, characterized in that said antimicrobial gel further comprises at least one silver salt, and at least one (optionally silver release-enhancing) hydrophilic component. Said antimicrobial gels may, inter alia, be produced from the compositions of the present invention, for instance through crosslinking the at least one alkenyl- and/or alkynyl-substituted polysiloxane and the at least one polysiloxane having silicon-bonded hydrogen atoms. The crosslinking may be effected through reacting the at least one alkenyl- and/or alkynyl-substituted polysiloxane and the at least one polysiloxane having silicon-bonded hydrogen atoms, for instance using, in an embodiment of the present invention, curing. Curing may be carried out under a various different conditions depending on the components of the composition, as well as on the desired properties of the resultant gel. In an additional embodiment, the curing may inter alia be carried out at between 40 and 140 degrees Centigrade, preferably between 60 and 130 degrees. In yet another embodiment, the timeframe during which the curing reaction is carried out may also vary depending on the above factors, but the crosslinking curing reaction may for instance be carried out for between 5 seconds and 2 hours, preferably between 10 seconds and 30 minutes, and more preferably between 30 seconds and 2 minutes.

In yet another embodiment as per the present invention, the antimicrobial gel may further comprise one or more excipients, for instance selected from siloxane-containing copolymers, siloxane polymer networks, and silica particles.

In a further embodiment, the antimicrobial gels of the present invention may comprise numerous different types of silver salts. Said silver salt may thus for instance be selected from the group comprising $Ag_2SO_4$, $Ag_2SO_3$, $AgNO_3$, $Ag_2CO_3$, $Ag_3PO_4$, silver zirconium, and/or organic silver salts, such as silver citrate, silver acetate, silver lactate and/or combinations or mixtures thereof. Various other compounds providing silver ions are conceivable and such compounds are also within the spirit of the present invention. In an embodiment of the present invention, the silver salt concentration may range from approximately 1% to 30%, and preferably from approximately 2% to 20%.

In an additional embodiment of the present invention, the antimicrobial gels of the present invention may comprise at least one (silver release-enhancing) hydrophilic component, inter alia selected from the group comprising mono- di- and/or polysaccharides, sugar alcohols, polyols, polyethers, polyesters, polyamides and/or polymers comprising pendant carboxylic acid groups and/or pendant sulphonate groups, but other hydrophilic polymers and molecules are also within the scope of the invention. In a further embodiment, the at least one hydrophilic component, which may enhance silver release, may be for instance be selected from the group comprising glucose, xylitol, sorbitol, mannitol, cyclodextrins, cellulose, hemicellulose, carboxymethylated cellulose, chitosan, dextran, chitin, amylose, amylopectin, polyethylene glycol, polypropylene glycol, copolymers of polyethylene glycol and polypropylene glycol, polyglycerol, poly(acrylic acid), copolymers of acrylic acid and $C_{10}$-$C_{30}$ alkyl acrylate, poly(acrylamide), maleic anhydride polymers and copolymers, carboxy methyl cellulose, methyl cellulose, hydroxymethylpropylcellulose, ethylcellulose, carboxyethylcellulose, hydroxypropylcellulose, hydroxyethylcellulose, carboxymethylcellulose, cellulose alkyl sulfonate, polystyrene sulphonates, vinyl acids and vinyl alcohols. In yet another embodiment, the (silver release-enhancing) hydrophilic component is preferably present in a concentration that ranges from approximately 3% to 40% (w/w), and more preferably from 4% to 30%.

The silver-releasing properties of the antimicrobial gels naturally have a significant impact on the overall antimicrobial effects seen when utilizing the gel and other aspects of the present invention in for instance a clinical setting. The amount of silver ions released from the prototypes may be investigated, in accordance with embodiments of the present invention, using a test method based on measurements of silver release from an antimicrobial gel and/or an antimicrobial wound dressing, using a two-compartment model. A piece of the prototype gel/dressing (d=20 mm, area 3.14 $cm^2$) was placed without release film on the membrane of a cell culture insert (pore size 8.0 µm), placed in a 6-well plate containing 4 mL sodium nitrate ($NaNO_3$, 0.15 M). The plates were incubated at 35° C. and the silver ion concentration was determined in the medium using a silver electrode. When the concentration was to be determined during several days, the samples were placed in fresh $NaNO_3$ after each measurement. The total silver concentration may also be determined using atomic absorption spectroscopy (AAS), if the medium is not compatible with the silver electrode (e.g. simulated wound fluid (SWF)), as well as other suitable methods.

As per one embodiment in line with the present invention, the antimicrobial gels may inhibit microbial growth, defined using inter alia the corrected zone of inhibition (CZoI) or the two-compartment test methods, over various time frames. The two-compartment test method involves culturing bacteria in 6-well plates, and, when evaluating the antimicrobial efficacy, placing dressing pieces (20 mm) in co-culture inserts (the porous membrane in the cell culture insert is detached so that the dressing has full contact with the bacterial culture). Bacteria are cultured in chemical simulated wound fluid, cSWF (NaCl 2.922 g, NaOHCO3 1.68 g, KCl 0.149 g, COCl2×2H2O 0.184 g, bovine albumin 16.5 g, in 500 ml Super Q water, pH 8.49. Initial concentration of the test organism is approximately $10^6$ CFU/ml prior to adding the test sample. The plates are incubated with agitation (100 rpm) and samples are withdrawn after specified times. The number of viable counts of the test organism is determined with standard surface plate count method and the amount of antimicrobials released is analyzed with relevant methodology, e.g. atomic absorption spectroscopy (AAS) for heavy metals. For release studies, the method can be used only with desired test fluid and no bacteria present.

The CZoI method involves placing a piece of wound dressing (d=20 mm) on an agar surface (Muller Hinton agar (MH agar)) in 25 ml/9 cm plates that produce an agar depth of 4 mm, which has been seeded with the test microorganism (*Pseudomonas aeruginosa*, ATCC 15442, and *Staphylococcus aureus*, ATCC 6538). Diffusion of antimicrobial agent into the agar results in inhibition of growth, which appears as a clear zone on the agar. The corrected zone of inhibition is determined as the diameter of the whole inhibition zone minus the size of the dressing.

The CZoI associated with the antimicrobial gels of the present invention may be, inter alia, approximately at least 2 mm at 24 h and approximately at least 2 mm at 48 h. Further in accordance with the invention, the accumulated silver release from the antimicrobial gels may amount to at least 0.3% of the total silver content after 24 h, and at least 0.5% of the total silver content after 48 h. In further embodiments of the present invention, the antimicrobial effects mediated by the antimicrobial gels of the present invention, as evaluated using the two-compartment model, may be in the order of at least one log, preferably at least two logs, and more preferably at least three logs.

An additional, standard method for evaluating the antimicrobial efficacy of the products as per the present invention is a modified version of ISO 22196:2007, i.e. a so called antimicrobial contact method. Briefly, the method encompasses covering a 5×5 cm sample piece with a thin layer of inoculum, incubating for a specific time period (commonly 24 h) before determining the number of viable test organisms. Test organism viability may be carried out as follows: shake method using neutralization buffer, plating, incubation, and plate count method. The minor deviations from the reference method in this case are that the inoculum used contains agar agar (3 g/l) and nutrient broth (5%). The test samples were inoculated with 1 ml inoculum containing approximately $1.2-3.0 \times 10^6$ CFU/ml.

Using the above-described, modified ISO method, the antimicrobial products of the present invention caused more than 3 log reductions in *P. aeruginosa* (ATCC 15442) viability.

The adhesion properties exhibited by the gel of the present invention are naturally highly important both for the actual antimicrobial efficacy and for the patient comfort and compliance. Thus, in accordance with the present invention, the antimicrobial gels may have an adhesion with steel of between 0.1 and 2 N, preferably between 0.1 and 1 N, and most preferably between 0.1 and 0.5 N. The determination of the adhesion is in this instance carried out in accordance with ASTM Internationals' standard D3330/D3330M-04, method F, but other suitable methods and standards may also be utilized. The antimicrobial gel may be combined with or incorporated into a dressing prior to application to a patient, but it is also within the spirit of the invention to apply the antimicrobial gel directly to a patient in need thereof.

In further embodiments of the present invention, the antimicrobial silicone gels of the present invention can be prepared in the form of layers and/or surface having different thicknesses, morphologies, patterns, functionalities, or the like, using any suitable technique, for instance extruding, calendering, molding, brushing, spraying, casting, coating, and/or application by hand. In yet another embodiment, the silicone gel may be preformed by casting and curing the gel-forming antimicrobial composition on a substrate. In further embodiments as per the invention, the layer and/or surfaces comprising the gel of the present invention may be in any geometric form, for instance dots, circles, networks, continuous configurations, discontinuous configurations, perforated layers and/or surfaces, and the like.

In accordance with further embodiments of the present invention, the substrate on which the antimicrobial gel is to be applied in order to create a wound dressing comprising the antimicrobial gel may be any surface that will generate the desired properties. The substrate may inter alia be selected from the group comprising inter alia a wound dressing, an ostomy dressing, ostomy baseplate, incision film, surgical drape, a patch, a bandage, a band-aid, a plaster, an adhesive, an adhesive tape, an adhesive plaster, a sticking-plaster, or a court-plaster, and/or any combination thereof. Further, the substrate may also be a component for the manufacture of any one of the above substrates and/or wound dressings, for instance a film, a textile, a foam, a non-woven film, a fiber network, a knitted fabric, or the like. Thus, in additional embodiments, the substrates and/or the wound dressings of the present invention may comprise textiles, films, foams, non-woven films, fiber networks, foams, knitted fabrics, and the like.

Suitable substrates in accordance with further embodiments of the present invention may comprise polyesters, polyethylenes, polypropylenes, polybutylenes, polymethylpentenes, polyolefins, polyvinyl acetates, polyvinyl chloride derivatives, polyethylene-vinyl acetate (EVA) and its copolymers, polyvinyls, polyvinyl alcohol, polyvinylbutyral, polyvinyl formal, polyacrylonitrile, polyurethanes and polyurethane-ureas, polystyrenes and their copolymers, epoxy and phenolic plastics, polyacrylic and polyacrylates derivatives, cellulose-based films, polyimides, polyamides, silicone elastomers, polyphenyl sulfide, polycarbonates, phenoplastes, fluorinated polymers, polyoxymethylenes, polyphenylene oxides, polysulfones, polysaccharide-based materials, and/or silicones, and/or any combination thereof.

As per one further aspect, the present invention pertains to an antimicrobial gel wherein said antimicrobial gel is formed by creating at least one covalent bond between at least one an alkenyl and/or alkynyl moiety of a first polysiloxane and at least one Si—H (i.e. a silicon-bonded hydrogen atom) moiety of second polysiloxane, said antimicrobial gel further comprising at least one hydrosilylation catalyst, at least one silver salt, and at least one (silver release-enhancing) hydrophilic component, wherein said at least one hydrophilic component makes said antimicrobial gel swell at least 5% (wt/wt) after 24 hours in Solution A, as measured by the free swell absorption method. Further in accordance with additional embodiments as per the present invention, the swelling may be at least 10% (wt/wt) after 24 hours in Solution A, or at least 20% (wt/wt) after 24 hours in Solution A, or at least 20% (wt/wt) after 24 hours in Solution A, or at least 30% (wt/wt) after 24 hours in Solution A, or at least 40% (wt/wt) after 24 hours in Solution A, or at least 50% (wt/wt) after 24 hours in Solution A, or at least 75% (wt/wt) after 24 hours in Solution A, or at least 100% (wt/wt) after 24 hours in Solution A, or at least 150% (wt/wt) after 24 hours in Solution A, or at least 200% (wt/wt) after 24 hours in Solution A, or at least 300% (wt/wt) after 24 hours in Solution A, or at least 400% (wt/wt) after 24 hours in Solution A, or at least 500% (wt/wt) after 24 hours in Solution A, or at least 600% (wt/wt) after 24 hours in Solution A, or at least 700% (wt/wt) after 24 hours in Solution A or at least 800% (wt/wt) after 24 hours in Solution A or any other lower or higher value, and any interval created by the above figures e.g. from 5% (wt/wt) to 800% (wt/wt) after 24 hours in Solution A.

Optionally, the swelling may be measured at different time points, for instance at 48 hours or at 72 hours, and also at these time points the swelling may be at least 10% (wt/wt) after 24 hours in Solution A, or at least 20% (wt/wt) after 24 hours in Solution A, or at least 20% (wt/wt) after 24 hours in Solution A, or at least 30% (wt/wt) after 24 hours in Solution A, or at least 40% (wt/wt) after 24 hours in Solution A, or at least 50% (wt/wt) after 24 hours in Solution A, or at least 75% (wt/wt) after 24 hours in Solution A, or at least 100% (wt/wt) after 24 hours in Solution A, or at least 150% (wt/wt) after 24 hours in Solution A, or at least 200% (wt/wt) after 24 hours in Solution A, or at least 300% (wt/wt) after 24 hours in Solution A, or at least 400% (wt/wt) after 24 hours in Solution A, or at least 500% (wt/wt) after 24 hours in Solution A, or at least 600% (wt/wt) after 24 hours in Solution A, or at least 700% (wt/wt) after 24 hours in Solution A or at least 800% (wt/wt) after 24 hours in Solution A or any other lower or higher value, and any interval created by the above figures e.g. from 5% (wt/wt) to 800% (wt/wt) after 24 hours in Solution A.

As abovementioned, the free swell absorption method is utilized to determine the swell properties. The free swell absorption method is carried out approximately as follows.

A suitable volume of Solution A is prepared. 1 liter is for instance prepared according to the following protocol:

Dissolve 8.298 g of sodium chloride (NaCl) and 0.368 g of calcium chloride dihydrate ($CaCl_2.H_2O$) in deionised water and fill up to 1 liter in a volumetric flask.

The first step of the free swell absorption method (which is a standard test method denoted EN 13726-1) involves cutting or punching a test piece of 5×5 cm of the product (for instance the antimicrobial gel) to be tested. In case of cavity dressings, use 0.2 gram. Second, condition the test piece at 23±2° C. and (50±2) % RH and subsequently weigh the sample and place it in a Petri dish. Add a quantity of Solution A warmed to 37±1° C. corresponding to 40 times the mass of the sample, ±0.5 g. Transfer to the oven and allow it to stand for the selected time, e.g. 24 h, at 37±1° C. Then, by using forceps, suspend the sample for 30 s by the corner or by one end as appropriate, carefully blot the sample to remove excess fluid, and then weigh it. Repeat the procedure for another nine samples, in order to obtain statistical significance.

Finally, express the absorptive capacity as the average mass (g) of solution retained per 100 cm$^2$ (as presented to the wound), per g of sample or in percentage of the sample weight.

In one embodiment, the at least one silver-release enhancing hydrophilic component of the antimicrobial gel is selected from a group comprising mono- di- and/or polysaccharides, sugar alcohols, polyols, polyethers, polyesters, polyamides and/or polymers comprising pendant carboxylic acid groups and/or pendant sulphonate groups. In a further embodiment, the at least one silver salt, that mediated the antimicrobial effect, is selected from the group comprising $Ag_2SO_4$, $Ag_2SO_3$, $AgNO_3$, $Ag_2CO_3$, $Ag_3PO_4$, silver zirconium, and/or organic silver salts, such as silver citrate, silver acetate, silver lactate and/or combinations or mixtures thereof.

In additional embodiments, the antimicrobial gel may comprise one or more excipients selected from the group comprising siloxane-containing copolymers, siloxane polymer networks, and silica particles.

Microbial inhibition may naturally be carried out using numerous different techniques, for instance through corrected zone of inhibition (CZoI) tests. The antimicrobial gels as per the present invention may exert an antimicrobial effect, in terms of CZoI, of at least 2 mm at 24 h and at least 2 mm at 48 h, and, in yet another embodiment, the accumulated silver release from the antibacterial gel may amount to at least 0.3% of the total silver content after 24 h, or may amount to at least 0.5% of the total silver content after 48 h.

Further as per the aspects and embodiments of the present invention, the at least one (optionally silver release-enhancing) hydrophilic component may cause the antimicrobial gels and compositions in accordance with the present invention to swell at least 5% (wt/wt) after 24 h in Solution A in accordance with the free swell absorption method, or it may cause the antimicrobial gels and compositions to swell at least 10% after 72 h in Solution A in accordance with the free swell absorption method.

Thus, another aspect of the present invention pertains to antimicrobial dressings inhibiting microbial growth and comprising the antimicrobial gels of the present invention may be highly useful in various contexts, it may for instance be applied in a professional clinical setting, either by a medical professional or by the patient, or in consumer product setting. The antimicrobial dressing may in accordance with an embodiment of the invention relate to any type of dressing with utility as a substrate for the antimicrobial gel, for instance a wound dressing, an ostomy dressing, ostomy baseplate, incision film, surgical drape, a patch, a bandage, a band-aid, a plaster, an adhesive, an adhesive tape, an adhesive plaster, a sticking-plaster, or a court-plaster, and any combination thereof.

The antimicrobial gel naturally confers its antimicrobial properties to the antimicrobial dressings of the present invention, but also the dressing as such can be optimized vis-à-vis for instance shape and/or morphology from an antimicrobial efficacy perspective. Thus, the antimicrobial dressings of the present invention may be adjusted to suit specific purposes, both in terms of physical appearance, physical properties, as well as in terms of constituents and chemical properties. The silver-releasing properties of the antimicrobial dressings as such naturally have a significant impact on the overall antimicrobial effects seen when utilizing the dressings in for instance a clinical setting. Hence, further in accordance with the invention, the accumulated silver release from the antimicrobial dressings of the present invention may amount to at least 0.3% of the total silver content after 24 h, and at least 0.5% of the total silver content after 48 h.

The adhesion properties exhibited by the dressings of the present invention logically depends on the adhesive properties of the antimicrobial gel comprised in the dressing. Again, the adhesion properties are naturally highly important both for the actual antimicrobial efficacy and for the patient comfort and compliance. The antimicrobial dressings of the present invention growth may be highly useful in various contexts, it may for instance be applied in a professional clinical setting, either by a medical professional or by the patient, or in consumer product setting.

The antimicrobial gels of the present invention may be prepared using a multitude of methods or combinations of method steps, in accordance with yet another aspect of the present invention, inter alia a method comprising an initial step of mixing a first suitable polysiloxane and at least one (silver release-enhancing) hydrophilic component, followed by heating of the obtained mixture until the hydrophilic component is molten. The mixture obtained after the melting step may then be mixed with a silver salt and subsequently with a second suitable polysiloxane. Finally, the mixture is cured in the presence of a catalyst, in an embodiment for instance Pt and/or Pd, and/or any other catalyst suitable for the preparation of antimicrobial gels. In a further embodiment of the present invention, the curing may inter alia be carried out at between approximately 40 and 140 degrees Centigrade, preferably between 60 and 130 degrees. In yet another embodiment, the timeframe during which the curing reaction is carried out may also vary depending on the above factors, but the crosslinking curing reaction may for instance be carried out for between 5 seconds and 2 hours, preferably between 10 seconds and 30 minutes, and more preferably between 30 seconds and 2 minutes. Naturally, the above steps may be performed simultaneously or sequentially or in any combination of sequential steps. In yet another embodiment of the present invention, the at least one silicone polymer network may be mixed with the mixture comprising the first polysiloxane and the molten release-enhancing hydrophilic component either prior to the addition of the silver salt or after.

In a further embodiment in accordance with the present invention, methods for preparing the antimicrobial gels may comprise the steps of mixing at least one alkenyl- and/or alkynyl-substituted polysiloxane, at least one catalyst, and silica particles, followed by subsequently adding silver salt paste to the mixture, forming a component A (FIG. 1). The silver paste may for instance comprise a polymer network and a suitable silver salt, for instance silver sulfate. A B component may be formed through mixing at least one alkenyl- and/or alkynyl-substituted polysiloxane, at least one CL comprising silicon-bonded hydrogen atoms, and at least one CE comprising silicon-bonded hydrogen atoms. Thereafter, a silver-release enhancing hydrophilic component is mixed with the mixture, optionally after heating and/or melting the silver-release enhancing hydrophilic component. Finally, component A and component B are mixed together prior to coating of a suitable medical substrate, inter alia any type of wound dressing in accordance with the present invention, and the preparation is finalized through curing the mix into an antimicrobial gel. Naturally, the above steps may be performed simultaneously or sequentially or in any combination of sequential steps. The above-described embodiment may be suitable for preparation of antimicrobial gels and wound dressing on a manufacturing scale, as the process steps are optimized vis-à-vis production settings and various important process parameters. Prior to curing the antimicrobial gel, said composition may naturally be applied in any pattern, structure, configuration, and/or morphology to a suitable substrate, e.g. a wound dressing, in order to further optimize the preparation process.

In additional embodiments of the present invention, methods for preparing antimicrobial products, such as antimicrobial gels and/or dressings, may comprise initial preparation of three mixtures, either simultaneously or sequentially or in any combination. Said three mixtures may comprise (i) at least one alkenyl- and/or alkynyl-functional polysiloxane, at least one hydrosilylation catalyst and, optionally, silica particles, (ii) at least one alkenyl- and/or alkynyl-functional polysiloxane, at least one CE and/or at least one CL, and, optionally, silica particles, and (iii) at least one silver salt and at least one siloxane-containing copolymer. Subsequently, at least one silver-release enhancing hydrophilic component is mixed with mixture (i) and/or mixture (ii), followed by optionally heating the obtained mixture(s) to which the silver-release enhancing hydrophilic component was added, in order to melt the silver-release enhancing hydrophilic component. The resulting mixtures are thereafter mixed and, after optional coating of a suitable substrate, cured, thus creating either an antimicrobial gel and/or an antimicrobial dressing, in accordance with the present invention.

In further embodiments in accordance with the present invention, the method for preparing the antimicrobial gels may comprise mixing at least one alkenyl- and/or alkynyl-substituted polysiloxane, at least one catalyst, and silica particles, in order to form a component A. A component B may be formed through mixing at least one alkenyl- and/or alkynyl-substituted polysiloxane, at least one CL comprising silicon-bonded hydrogen atoms, and at least one CE comprising silicon-bonded hydrogen atoms. Further, a silver salt paste may be prepared through mixing a polymer network with a suitable silver salt, for instance silver sulfate. Subsequently, component A is mixed with a release-enhancing hydrophilic component, and heated if necessary, prior to addition and mixing of the silver paste, and finally addition and mixing of component B, followed by optional coating of a substrate and curing, in order to form a antimicrobial gel and/or wound dressing in accordance with the present invention.

In another embodiment of the present invention pertaining to the preparation of an antimicrobial gel, and an antimicrobial substrate, a first component is prepared, comprising inter alia an alkenyl- and/or alkynyl-substituted polydiorganosiloxane, a silver salt, silica particles, a catalyst, and an inhibitor. Subsequently, said first component is mixed in a speedmixer until the silica particles have been thoroughly dispersed, wherein after a second component, comprising an alkenyl- and/or alkynyl-substituted polydiorganosiloxane, chain extenders, and crosslinkers, is added, followed by speedmixing and subsequent application on a suitable substrate. Finally, the substrate and the antimicrobial gel is cured, for instance for approximately 10 minutes at 120 degrees, resulting in a product with antimicrobial properties. As per other embodiments and aspects of the present invention, antimicrobial gels may be prepared using numerous additional constituents, in order to achieve certain effects pertaining to inter alia increased silver release, optimized tack, viscosity, mechanical strength, and/or patient comfort and compliance.

The antimicrobial dressings of the present invention may be prepared using a multitude of methods or combinations of method steps, inter alia a method comprising, as per an embodiment, an initial step of mixing a first suitable polysiloxane and at least one hydrophilic component, followed by heating of the obtained mixture until the at least one (optionally silver release-enhancing) hydrophilic component is molten. The mixture obtained after the melting step may then be mixed with a silver salt and subsequently with a second suitable polysiloxane. Thereafter, the mixture may be applied to a substrate, in various suitable patterns, morphologies, and thicknesses, followed by curing of the substrate and the applied mixture in the presence of a suitable catalyst, for instance, in an embodiment, Pt and/or Pd, and/or any other suitable catalyst. In a further embodiment, the curing may inter alia be carried out at between 40 and 140 degrees Centigrade, preferably between 60 and 130 degrees. In yet another embodiment, the timeframe during which the curing reaction is carried out may also vary depending on the above factors, but the crosslinking curing reaction may for instance be carried out for between 5 seconds and 2 hours, preferably between 10 seconds and 30 minutes, and more preferably between 30 seconds and 2 minutes.

Naturally, the above steps may be performed simultaneously or sequentially or in any combination of sequential steps, for instance may the mixture, as per an embodiment, be applied to the substrate prior to the mixing with the second polysiloxane. In a further embodiment, the substrate utilized for the preparation of antimicrobial dressings may be any type of dressing with utility as a substrate for the antimicrobial gel, for instance wound dressing, an ostomy dressing, ostomy baseplate, incision film, surgical drape, a pad, a patch, a bandage, a band-aid, a plaster, an adhesive, an adhesive tape, an adhesive plaster, a sticking-plaster, or a court-plaster. According to another embodiment, the at least one silicone polymer network may again be mixed with the mixture comprising the first polysiloxane and the molten release-enhancing hydrophilic component either prior to the addition of the silver salt or after.

In yet another embodiment, antimicrobial dressings are prepared through initially heating at least one silver-release enhancing component, at least one alkenyl- and/or alkynyl-substituted polydiorganosiloxane, at least one hydrosilylation catalyst, and, optionally, silica particles, followed by mixing of said components, in order to obtain an emulsion. Subsequently, the emulsion is mixed with a silver paste comprising at least one silver salt and a polysiloxane—polyether copolymer network. Finally, the silver-containing emulsion is blended with a mix of at least one alkenyl- and/or alkynyl-substituted polydiorganosiloxane and at least one crosslinker polysiloxane comprising silicone-bonded hydrogen, followed by application to a suitable substrate, and curing.

In an additional embodiment in accordance with the present invention, antimicrobial dressings are prepared mixing at least one silver-release enhancing hydrophilic component, for instance particles of a suitable sugar alcohol, at least one alkenyl- and/or alkynyl-substituted polydiorganosiloxane, and at least one hydrosilylation catalyst, in order to form a suspension. The suspension if subsequently mixed with a silver paste comprising at least one silver salt and a polysiloxane—polyether copolymer network. Finally, the silver-containing emulsion is blended with a mix of at least one alkenyl- and/or alkynyl-substituted polydiorganosiloxane and at least one crosslinker polysiloxane comprising silicone-bonded hydrogen, followed by application to a suitable substrate, and curing.

Further as per the present invention, antimicrobial dressings can be prepared through mixing at least one alkenyl- and/or alkynyl-substituted polydiorganosiloxane and at least one hydrosilylation catalyst to form a component A. Subsequently, at least one alkenyl- and/or alkynyl-substituted polydiorganosiloxane is mixed with a polysiloxane comprising silicon-bonded hydrogen atoms to form a component B, followed by continuous mixing of components A and B by joining two streams comprising component A and component B, respectively. A suitable silver salt and additional excipients, for instance a silver-release enhancing hydrophilic component, is subsequently added, inter alia in the form of a powder. Finally, the obtained mixture is applied to a substrate and cured, in order to generate an antimicrobial dressing as per the present invention.

An additional aspect in accordance with the present invention relates to use of the antimicrobial gel in a product for treating wounds, burns, cuts, bruises, and the like, in various settings and for various purposes.

It shall be understood that the above described exemplifying embodiments can be modified without departing from the scope of the invention, inter alia with respect to the described constituents, materials, and process parameters applied. The invention will now be further exemplified with the enclosed examples, which naturally also can be modified without departing from the scope of the invention.

EXAMPLES

The following materials were used in the preparation of the antimicrobial compositions and gel of the present invention. Vinyl 1000 A dimethylvinyl siloxy-terminated polydimethylsiloxane, having a viscosity of 1000 mPa·s containing 0.18-0.26 wt % vinyl, the chain extender trimethylsiloxy-terminated methylhydrogen polydimethylsiloxane, having a viscosity of 25-35 m Pa·s containing 25-30 mol % MeHSiO, and the crosslinker trimethylsiloxy-terminated methylhydrogen polydimethylsiloxane having a viscosity of 25-35 m Pa·s containing 25-30 mol % as MeHSiO were obtained from ABCR GmbH & Co. KG (AB109358, AB109366, and AB109380 respectively). Platinum catalyst, Cat 511, was obtained from Hanse Chemie, silica, H15, was obtained from Wacker Chemie, mannitol was obtained from Sigma Aldrich, Polyethyleneglycol 3000 S was obtained from Clariant (referred to as PEG 3000 below), Pluriol 6005 and Pluriol 8005 were obtained from BASF (referred to as PEG 6000 and PEG 8000, respectively), silver sulfate ($Ag_2SO_4$) was obtained from Alpha Aesar (stock number 11417), and Velvesil plus and Velvesil 125 were obtained from Momentive.

Example 1

Silicone Gel Compositions

Silicone gel compositions were prepared by mixing together the components in the amounts listed below. First, a silicone gel formulation was prepared, which was utilized together with the antimicrobial and release-enhancing additives.

The silicone gel was prepared in a two-component system in order to separate the catalyst and the crosslinker/chain extender prior to the curing process.

Component A may, inter alia, comprise the following components:
1. Vinyl terminated PDMS (Vin 1000) and Silica (HDK, H15) were mixed in a jar and blended for 5 minutes with a Speedmixer.
2. The catalyst was added and the mixture was blended for 2 min in the Speedmixer Component B may, inter alia, comprise the following components:
1. The polymers, including Vin 1000, CL, and CE, were mixed in a jar and blended 2 min in the Speedmixer.

TABLE 1

| Component A | | | Component B | | |
|---|---|---|---|---|---|
| Vin 1000 | Silica HDK H15 | Catalyst 511 | Vin 1000 | CL AB 109380 | CE AB 109366 |
| 0.479 (47.9 g) | 0.02 (2 g) | 0.001 (0.1 g) | 0.197 (19.7 g) | 0.003 (0.3 g) | 0.3 (30 g) |

Based on the above outlined base formulation, two antimicrobial formulations were prepared.

Example 2

Silicone Formulation with Silver Sulfate and PEG

A formulation was prepared using a method comprising the following steps:
1) Adding a silicone component A (3.75 g), in accordance with example 1, in a jar with PEG 8000 (3 g).
2) heating at 80° C. until the PEG is molten. The phases are subsequently mixed in a Speedmixer until an emulsion is formed (a timeframe of approximately 2 min).
3) preparing a paste of $Ag_2SO_4$ (3 g) and Velvesil plus (1.5 g) by mixing the silver powder and the Velvesil in a jar, and blending with the Speedmixer.
4) adding the silver paste to component A and mix
5) adding inhibitor (0.015 g) to silicone B and mix
6) add silicone component B (3.75 g)

TABLE 2

| PEG 8000 | Velvesil Plus | $Ag_2SO_4$ | Silicone A | Silicone B | Inhibitor |
|---|---|---|---|---|---|
| 0.2 (3 g) | 0.1 (1.5 g) | 0.2 (3 g) | 0.25 (3.75 g) | 0.25 (3.75 g) | 0.001 (0.015 g) |

The above outlined steps may naturally, where applicable, be performed simultaneously or sequentially or in any combination of sequential steps.

Example 3

Silicone Formulation with Silver Sulfate and Mannitol

A formulation was prepared using a method comprising the following steps:
1) putting the silicone component A (3 g), in accordance with example 1, in a jar with mannitol (4.5 g).

2) mixing the phases in a Speedmixer until a suspension is formed (approximately 2 min).
3) preparing a paste of $Ag_2SO_4$ (3 g) and Velvesil plus (1.5 g) by mixing the silver powder and Velvesil in a jar and blending with the Speedmixer.
4) adding the silver paste to component A and mix
5) adding inhibitor (0.015 g) to silicone B and mix
6) adding the silicone component B (3.75 g)

TABLE 3

| Mannitol | Velvesil Plus | $Ag_2SO_4$ | Silicone A | Silicone B | Inhibitor |
|---|---|---|---|---|---|
| 0.3 (4.5 g) | 0.1 (1.5 g) | 0.2 (3 g) | 0.2 (3 g) | 0.2 (3 g) | 0.001 (0.015 g) |

The formulations were coated on a film substrate comprising polyurethane. Test pieces with a diameter of 20 mm were punched and subjected to antimicrobial testing according to the CZoI method and the two-compartment test method.

Example 4

Silicone Formulation with Silver Sulfate and CMC

A formulation was prepared using a method comprising the following steps:
1) putting the silicone component A (5.92 g), in accordance with example 1, in a jar with CMC Akucell AF 2781W (1.5 g).
2) mixing the phases in a Speedmixer until a suspension is formed (approximately 2 min).
3) to component A adding $Ag_2SO_4$ (1.5 g) and Velvesil plus (0.15 g) to the mixture and blending with the Speedmixer (approximately 2 minutes).
4) adding the silicone component B (5.92 g) to the mixture and mix in the speedmixer (approximately 2 minutes).

TABLE 4

| CMC | Velvesil Plus | $Ag_2SO_4$ | Silicone A | Silicone B |
|---|---|---|---|---|
| 0.10 (1.5 g) | 0.01 (0.15 g) | 0.10 (1.5 g) | 0.395 (5.92 g) | 0.395 (5.92 g) |

The formulations were coated on a film substrate comprising polyurethane. Test pieces with a diameter of 20 mm were punched and subjected to antimicrobial testing according to the CZoI method and the two-compartment test method.

Example 5

Addition of Silver Sulfate and CMC with the Addition of Silicone Polyether

1) To 80 g of component A of silicone gel (Dow Corning 7-9900) 10 g of silver sulfate and 10 g of CMC (Akucell 2781) was added and blended in a speed mixer for 2 min
2) To this mixture 0.2 g of silicone polyether (Dow Corning FZ 2233) was added and blended in the speed mixer for 2 min
3) To this mixture 80 g of component B (Dow corning 7-9900) was added and blended in the mixer.
4) The sample was left to cure at room temperature.
The sample cured to a gel.

Example 6

Addition of Silver Sulfate and CMC with the Addition of Silicone Polyether Crosspolymer 1) To 80 g of component A of silicone gel (Dow Corning 7-9900) 10 g of silver sulfate and 10 g of CMC (Akucell 2781) was added and blended in a speed mixer for 2 min
2) To this mixture 1 g of silicone polyether crosspolymer (Momentive, Velvesil plus) was added and blended in the speed mixer for 2 min
3) To this mixture 80 g of component B (Dow corning 7-9900) was added and blended in the mixer.
4) The sample was left to cure at room temperature.
The sample cured to a gel.

Example 7

Silver Release and Antimicrobial Effects

The antimicrobial effects of the antimicrobial gels of the present invention were evaluated for a number of differently formulated gels, as summarized in Table 5 below. Essentially no antimicrobial activity was detected when omitting the at least one (optionally silver release-enhancing) hydrophilic component (cf. samples 2N1 and 2N2 in Table 5 below). Additionally, hydrophilic components that do not at all enhance the swelling of the antimicrobial products as per the present invention analogously cause essentially no antimicrobial effects. Thus, it is clear that the swelling effects mediated by the hydrophilic components as per the present invention result in enhanced antimicrobial efficacy.

TABLE 5

| | ID | | | | | | | | | |
|---|---|---|---|---|---|---|---|---|---|---|
| | 2N1 | 2N2 | 3N1 | 3N6 | 3N8 | 5N6 | 7N4 | 9N4 | 9N5 | 9N8 |
| $Ag_2SO_4$ | 0.1 | 0.1 | 0.05 | 0.2 | 0.2 | 0.2 | 0.2 | 0.1 | 0.1 | 0.2 |
| PEG 3000 | | | 0.1 | 0.1 | 0.25 | | | | | |
| PEG 6000 | | | | | | | 0.2 | | | |
| PEG 8000 | | | | | 0.2 | | | | | |
| Velvesil plus | | 0.1 | 0.1 | 0.1 | 0.1 | 0.1 | | 0.1 | 0.1 | 0.1 |
| Velvesil 125 | | | | | | | 0.1 | | | |
| Mannitol | | | | | | | | 0.3 | | 0.3 |
| Sorbitol | | | | | | | | | 0.3 | |
| PDMS | 0.9 | 0.8 | 0.75 | 0.6 | 0.55 | 0.5 | 0.5 | 0.5 | 0.5 | 0.4 |

TABLE 5-continued

| | ID | | | | | | | | | |
|---|---|---|---|---|---|---|---|---|---|---|
| | 2N1 | 2N2 | 3N1 | 3N6 | 3N8 | 5N6 | 7N4 | 9N4 | 9N5 | 9N8 |
| Test results | | | | | | | | | | |
| CZoI 24 h (mm) | <1 | <1 | <1 | 3 | 5 | 6 | 3.5 | 4 | 5 | 6 |
| Total Ag Release 24 h (%) | 0 | 0 | 0.7 | 0.3 | 16 | 17 | 0.03 | 5 | 10 | 34 |
| Total Ag Release 48 h (%) | 0 | 0 | 0.8 | 0.8 | 27 | 34 | 0.07 | 7.5 | 12 | 54 |

Figure 3:
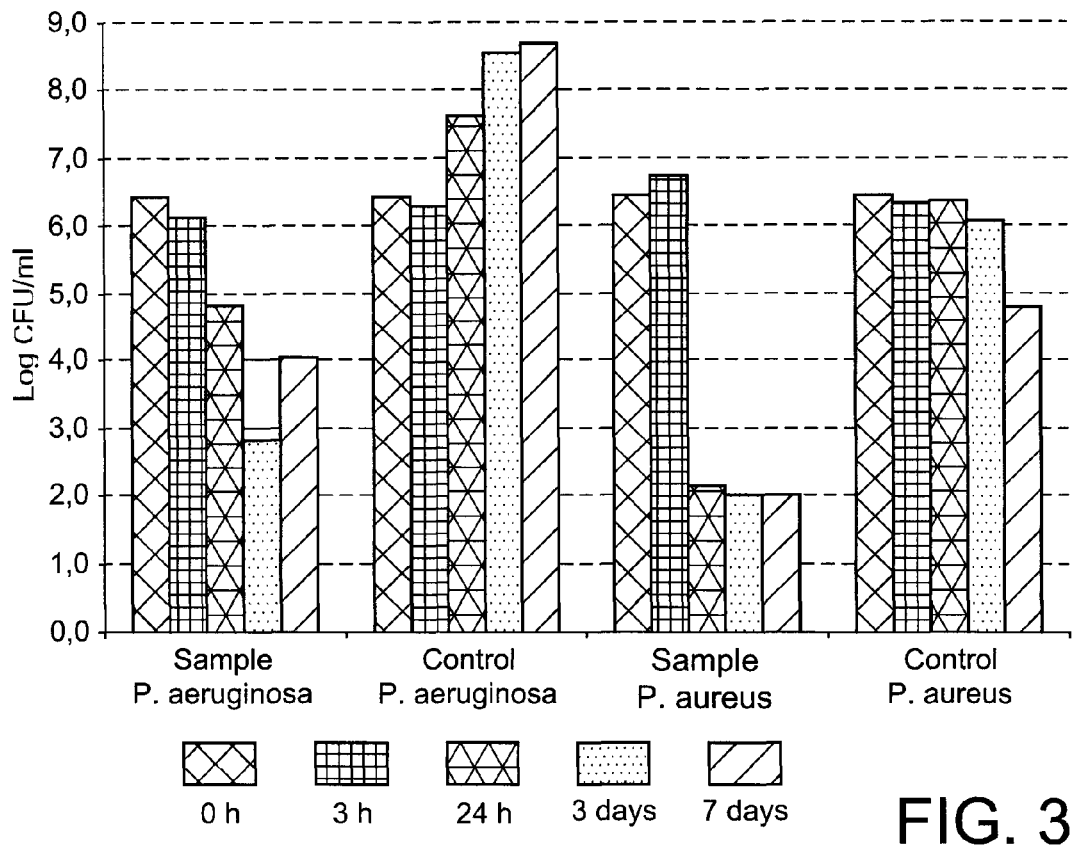
FIG. 3 illustrates the reduction of *P. aeruginosa* and *S. aureus* after exposure to the antimicrobial gels, and in particular formulation 5N6 disclosed below, of the present invention.

The antimicrobial gels prepared in accordance with the present invention displayed desirable properties both in terms of silver release over time and in terms of antimicrobial effects, with the antimicrobial efficacy being based on measurements of corrected zone of inhibition (CZoI) (Table 4), on the reduction of the number of colony-forming units (CFU) of *Pseudomonas aeruginosa* only (FIG. 4) and *Pseudomonas aeruginosa* and *Staphylococcus aureus* (FIG. 3), and on the modified ISO antimicrobial contact method. Briefly regarding the data presented in FIGS. 3 and 4, wound dressings comprising composition 5N6 were tested against two common infectious agents, i. e. *Pseudomonas aeruginosa* and *Staphylococcus aureus*. The samples were inoculated with $10^6$ bacteria and subjected to substrates coated with antimicrobial compositions of the invention. Comparisons of the sample and the control show the antimicrobial effect as log reductions over time, with the antimicrobial gels as per the present invention being able to reduce the number of colony forming units (CFUs) of *Staphylococcus aureus* from $10^6$ to at least $10^5$ in 24 h, or preferably from $10^6$ to at least $10^4$ in 24 h, or most preferably from $10^6$ to at least $10^3$ in 24 h.

Figure 4:
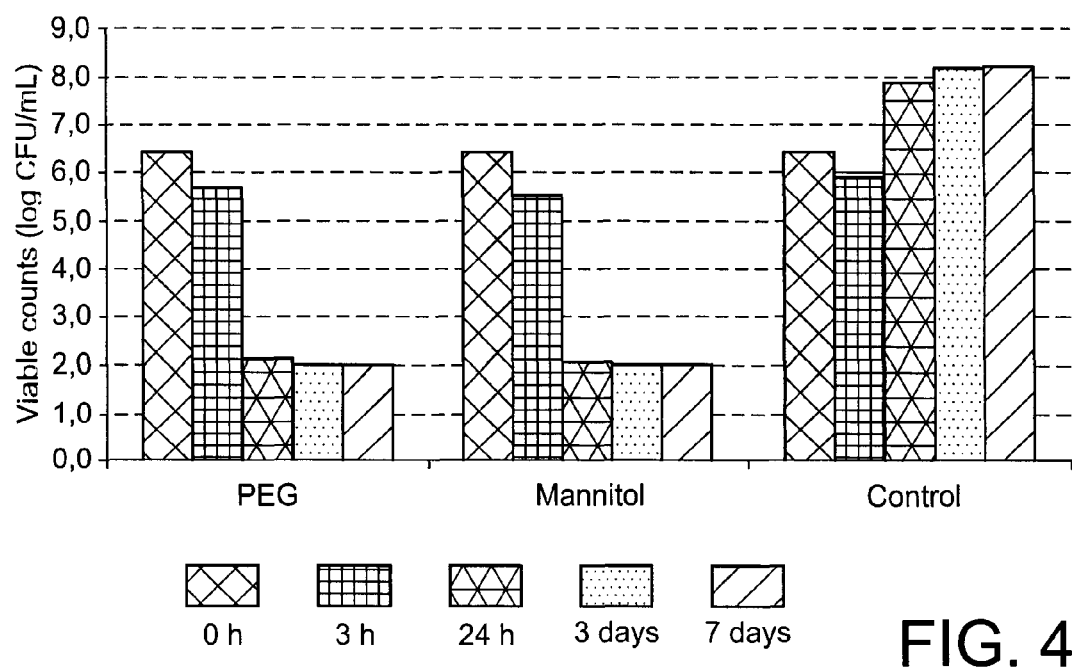
FIG. 4 illustrates the reduction of *P. aeruginosa* after exposure to selected antimicrobial gels of the present invention.
Figure 5:
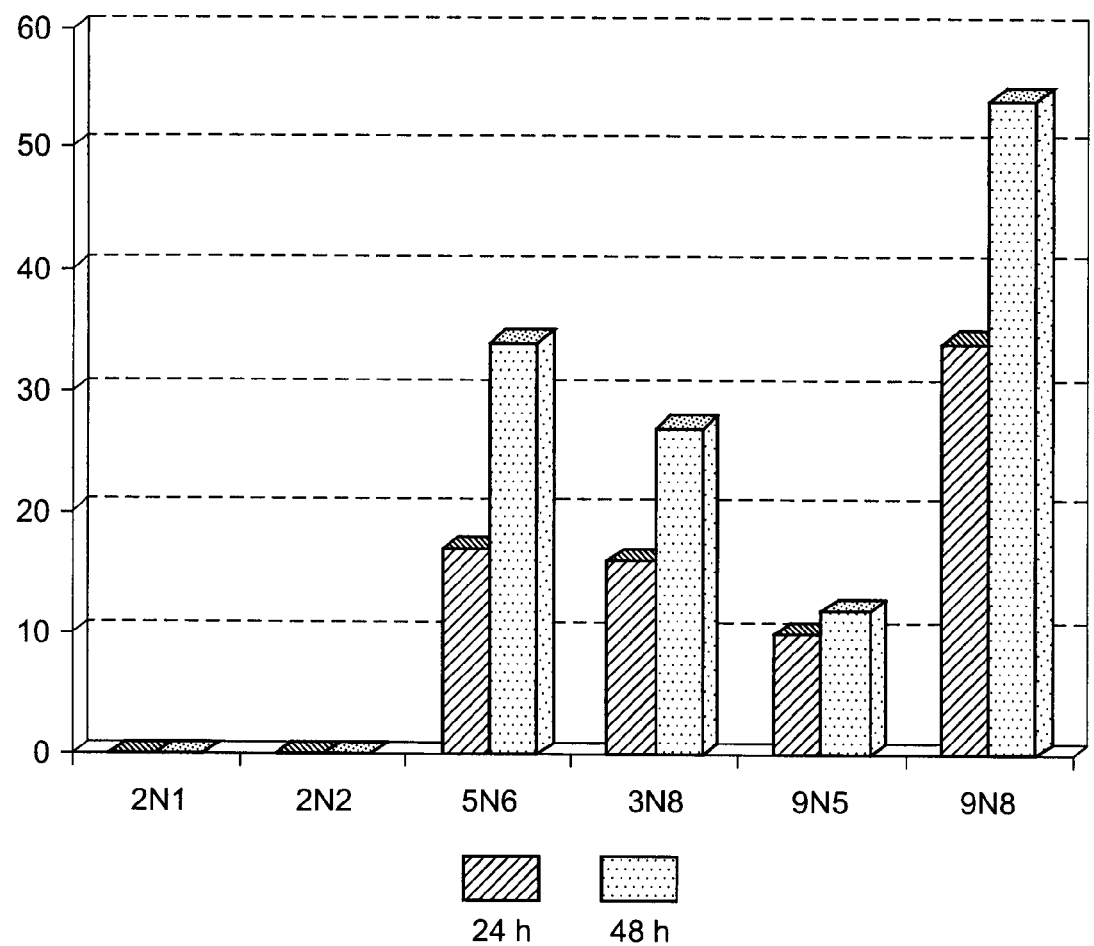
FIG. 5 illustrates the importance (for enhancing silver release) of the hydrophilic component (silver release is expressed in % of the total added mass of $Ag_2SO_4$ at 24 h and 48 h (from various samples in $NaNO_3$ solution)). The samples denoted 2N1 and 2N2 do not contain any (silver release-enhancing) hydrophilic component, as can be seen from Table 5.

FIG. 4 displays data resulting from two-compartment model tests on *P. aeruginosa*, based on antimicrobial gels in accordance with the present invention, comprising excipients such as PEG and mannitol. Substantial antimicrobial effects can be seen with both gels, with at least four logs reduction in CFU/ml over time frames as long as one week Example 8

Swelling Properties

The swelling properties of various antimicrobial gels and cross-linked compositions in accordance with the present invention were analyzed using the free swell absorption method. As can be seen from Table 6, the (optionally silver release-enhancing) hydrophilic components of the present invention mediate substantial swelling, leading to improved silver release and/or enhanced antimicrobial efficacy.

TABLE 6

| | | Swelling | | | |
|---|---|---|---|---|---|
| No | Sample Description | % 6 h | % 24 h | % 48 h | % 72 h |
| 1 | MAG11-B: 5% Pemulen TR-2 | 31% | 39% | 71% | 85% |
| 2 | MAG11-D: 10% Pemulen TR-2 | 64% | 60% | 73% | 72% |
| 3 | MAG11-G: 10% CMC 3281 | 114% | 125% | 143% | 135% |
| 4 | MAG11-H: 20% CMC 3281 | 279% | 326% | 353% | 360% |
| 5 | MAG11-I: 10% Mannitol | 53% | 62% | 69% | 67% |
| 6 | MAG11-J: 20% Mannitol | 55% | 66% | 69% | 61% |
| 7 | MAG11-K: 10% pestle Mannitol | 38% | 66% | 74% | 86% |

The invention claimed is:

1. An antimicrobial composition comprising at least one alkenyl- and/or alkynyl-substituted polysiloxane, at least one polysiloxane comprising silicon-bonded hydrogen atoms, and at least one hydrosilylation catalyst, wherein the composition further comprises at least one silver salt and at least one hydrophilic component, wherein the at least one hydrophilic component promotes release of the at least one silver salt such that the antimicrobial composition has an accumulated silver release of at least 0.3% of the total silver content in the initial antimicrobial composition after 24 hours, and wherein the at least one hydrophilic component makes the antimicrobial composition, when cross-linked, swell at least 5% (wt/wt) after 24 hours in a water solution containing 8.298 g/L of sodium chloride and 0.368 g/L of calcium chloride dihydrate, as measured by the free swell absorption method, wherein the at least one alkenyl- and/or alkynyl-substituted polysiloxane is covalently crosslinked to the at least one polysiloxane comprising silicon-bonded hydrogen atoms, thereby forming an antimicrobial gel.

2. The antimicrobial composition of claim 1, wherein the at least one hydrophilic component comprises a glucose, xylitol, sorbitol, mannitol, cyclodextrin, cellulose, hemicellulose, carboxymethylated cellulose, chitosan, dextran, chitin, amylose, amylopectin, polyethylene glycol, polypropylene glycol, copolymer of polyethylene glycol and polypropylene glycol, polyglycerol, poly(acrylic acid), copolymer of acrylic acid and $C_{10}$-$C_{30}$ alkyl acrylate, poly(acrylamide), maleic anhydride polymer, maleic anhydride copolymer, or carboxy methyl cellulose, methyl cellulose, hydroxymethylpropylcellulose, ethylcellulose, carboxyethylcellulose, hydroxypropylcellulose, hydroxyethylcellulose, carboxymethylcellulose, cellulose alkyl sulfonate, polystyrene sulphonate, vinyl acid, vinyl alcohol, or a mixture thereof.

3. The antimicrobial composition of claim 1, wherein the concentration of the at least one hydrophilic component is between 3% and 40% (w/w).

4. The antimicrobial composition of claim 1, wherein the antimicrobial composition further comprises between 1% and 5% (w/w) silica particles.

5. The antimicrobial composition of claim 1, wherein the silver salt concentration is between 1% and 30% (w/w).

6. The antimicrobial composition of claim 1, wherein the antimicrobial composition further comprises at least one siloxane-containing copolymer.

7. The antimicrobial composition of claim 6, wherein the at least one siloxane-containing copolymer comprises at least one siloxane polymer network, at least one siloxane polyether (SPE), or a mixture thereof.

8. The antimicrobial composition of claim 6, wherein the at least one siloxane-containing copolymer is present at a concentration of between 0.1% and 30% (w/w).

9. The antimicrobial composition of claim 7, wherein the at least one siloxane-containing copolymer is the at least one siloxane polymer network, wherein the at least one siloxane polymer network comprises a poly-ether-siloxane copolymer network.

10. The antimicrobial composition according to claim 1, wherein the at least one hydrophilic component comprises a mono-polysaccharide, di-polysaccharide, sugar alcohol, polyol, polyether, polyester, polyamide, polymer comprising a pendant carboxylic acid group, a polymer comprising a pendant sulphonate group, or a mixture thereof.

11. The antimicrobial composition of claim 1, wherein the at least one silver salt comprises $Ag_2SO_4$, $Ag_2SO_3$; $AgNO_3$, $Ag_2CO_3$, $Ag_3PO_4$, silver zirconium, silver citrate, silver acetate, silver lactate, or a mixture thereof.

12. The antimicrobial composition of claim 1, wherein the at least one hydrophilic component comprises a sorbitol, mannitol, polyethylene glycol, or carboxy methyl cellulose, or a mixture thereof.

13. An antimicrobial gel produced from a composition comprising at least one alkenyl- and/or alkynyl-substituted polysiloxane, at least one polysiloxane comprising silicon-bonded hydrogen atoms, and at least one hydrosilylation catalyst, wherein the composition further comprises at least one silver salt and at least one hydrophilic component, wherein the at least one hydrophilic component promotes release of the at least one silver salt such that the antimicrobial gel has an accumulated silver release of at least 0.3% of the total silver content in the initial antimicrobial gel after 24 hours, and wherein the at least one hydrophilic component makes the antimicrobial composition, when crosslinked, swell at least 5% (wt/wt) after 24 hours in a water solution containing 8.298 g/L of sodium chloride and 0.368 g/L of calcium chloride dihydrate, as measured by the free swell absorption method, wherein the gel is produced through crosslinking the at least one alkenyl- and/or alkynyl-substituted polysiloxane and the at least one polysiloxane comprising silicon-bonded hydrogen atoms.

14. The antimicrobial gel of claim 13, wherein the crosslinking of the polysiloxanes is carried out using curing.

15. The antimicrobial gel of claim 13, wherein the antimicrobial gel further comprises one or more excipients comprising a siloxane-containing copolymer, silica particle, or a mixture thereof.

16. The antimicrobial gel of claim 13, wherein the corrected zone of inhibition (CZoI) of microbial growth brought about by the antimicrobial gel is at least 2 mm at 24 h.

17. The antimicrobial gel of claim 13, wherein a circular sample of the antimicrobial gel, assessed using the two-compartment test method, having a diameter of about 20 mm and a coat weight of about 500 g/m$^2$, when exposed to 4 ml of bacteria-containing chemical simulated wound fluid at a temperature of 37° C., is able to reduce the number of colony forming units (CFUs) of *Staphylococcus aureus* from $10^6$ to at least $10^5$ in 24 h.

18. The antimicrobial gel of claim 13, wherein the gel has an adhesion with steel of between 0.1 and 2 N as measured by ASTM Internationals' standard D3330/D3330M-04, method F.

19. The antimicrobial gel of claim 13, wherein the at least one hydrophilic component comprises a glucose, xylitol, sorbitol, mannitol, cyclodextrin, cellulose, hemicellulose, carboxymethylated cellulose, chitosan, dextran, chitin, amylose, amylopectin, polyethylene glycol, polypropylene glycol, copolymer of polyethylene glycol and polypropylene glycol, polyglycerol, poly(acrylic acid), copolymer of acrylic acid and $C_{10}$-$C_{30}$ alkyl acrylate, poly(acrylamide), maleic anhydride polymer, maleic anhydride copolymer, or carboxy methyl cellulose, methyl cellulose, hydroxymethylpropylcellulose, ethylcellulose, carboxyethylcellulose, hydroxypropylcellulose, hydroxyethylcellulose, carboxymethylcellulose, cellulose alkyl sulfonate, polystyrene sulphonate, vinyl acid, vinyl alcohol, or a mixture thereof.

20. The antimicrobial gel of claim 13, wherein the concentration of the at least one hydrophilic component is between 3% and 40% (w/w).

21. The antimicrobial gel of claim 13, wherein the antimicrobial gel further comprises between 1% and 5% (w/w) silica particles.

22. The antimicrobial gel of claim 13, wherein the silver salt concentration is between 1% and 30% (w/w).

23. The antimicrobial gel of claim 13, wherein the antimicrobial gel further comprises at least one siloxane-containing copolymer.

24. The antimicrobial gel of claim 23, wherein the at least one siloxane-containing copolymer comprises at least one siloxane polymer network, at least one SPE, or a mixture thereof.

25. The antimicrobial gel of claim 23, wherein the at least one siloxane-containing copolymer is present at a concentration of between 0.1% and 30% (w/w).

26. The antimicrobial gel of claim 24, wherein the at least one siloxane-containing copolymer is the at least one siloxane polymer network, wherein the at least one siloxane polymer network comprises a poly-ether-siloxane copolymer network.

27. The antimicrobial gel according to claim 13, wherein the at least one hydrophilic component comprises a mono-polysaccharide, di-polysaccharide, sugar alcohol, polyol, polyether, polyester, polyamide, polymer comprising a pendant carboxylic acid group, a polymer comprising a pendant sulphonate group, or a mixture thereof.

28. The antimicrobial gel of claim 13, wherein the at least one silver salt comprises $Ag_2SO_4$, $Ag_2SO_3$; $AgNO_3$, $Ag_2CO_3$, $Ag_3PO_4$, silver zirconium, silver citrate, silver acetate, silver lactate, or a mixture thereof.

29. The antimicrobial composition of claim 13, wherein the at least one hydrophilic component comprises a sorbitol, mannitol, polyethylene glycol, or carboxy methyl cellulose, or a mixture thereof.

30. An antimicrobial dressing comprising the antimicrobial gel of claim 13.

31. The antimicrobial dressing of claim 30, wherein the antimicrobial gel is applied on a substrate.

32. The antimicrobial dressing of claim 30, wherein the dressing comprises a wound dressing, an ostomy dressing, ostomy baseplate, incision film, surgical drape, a patch, a bandage, a band-aid, a plaster, an adhesive, an adhesive tape, an adhesive plaster, a sticking-plaster, a court-plaster, or a combination thereof.

33. A method for preparing an antimicrobial gel of claim 13, comprising the following steps of:
 (a) preparing the three mixtures (i), (ii), and (iii), either simultaneously or sequentially or in any combination of (i), (ii), and (iii), comprising;
  (i) at least one alkenyl- and/or alkynyl-functional polysiloxane, at least one hydrosilylation catalyst and, optionally, silica particles;
  (ii) at least one alkenyl- and/or alkynyl-functional polysiloxane, at least one chain extender and/or at least one crosslinker, and, optionally, silica particles;
  (iii) at least one silver salt and at least one siloxane-containing copolymer;

(b) mixing at least one hydrophilic component with mixture (i) and/or mixture (ii), followed by optionally heating the mixture(s) to which the at least one hydrophilic component was added, in order to melt the at least one silver-release enhancing hydrophilic component;

(c) mixing mixture (iii) with mixture (i) and/or mixture (ii);

(d) mixing mixture (i) and mixture (ii); and (e) curing the mixture obtained in step (d), thereby obtaining the antimicrobial gel.

34. A method for preparing an antimicrobial dressing of claim 30, comprising the following steps of:
(a) preparing the three mixtures (i), (ii), and (iii), either simultaneously or sequentially or in any combination of (i), (ii), and (iii), comprising;
   (i) at least one alkenyl- and/or alkynyl-functional polysiloxane, at least one hydrosilylation catalyst and, optionally, silica particles;
   (ii) at least one alkenyl- and/or alkynyl-functional polysiloxane, at least one chain extender and/or at least one crosslinker, and, optionally, silica particles;
   (iii) at least one silver salt and at least one siloxane-containing copolymer;
(b) mixing the at least one hydrophilic component with mixture (i) and/or mixture (ii), followed by optionally heating the mixture(s) to which the at least one hydrophilic component was added, in order to melt the hydrophilic component;
(c) mixing mixture (iii) with mixture (i) and/or mixture (ii) U;
(d) mixing mixture (i) and mixture (ii);
(e) coating a substrate with the mixture obtained in step (d); and
(f) curing the mixture coated on the substrate of step (e), thereby obtaining the antimicrobial dressing.

35. The method of claim 34, wherein the substrate comprises a wound dressing, an ostomy dressing, an ostomy baseplate, an incision film, a surgical drape, a pad, a patch, a bandage, a band-aid, a plaster, an adhesive, an adhesive tape, an adhesive plaster, a sticking-plaster, a court-plaster, or a mixture thereof, or wherein the substrate is a component for production of any one of the above substrates, wherein the component for production comprises a film, a textile, a foam, a non-woven film, a fiber network, a knitted fabric, or a combination thereof.

36. A method for treating a burn, scar, bacterial infection, viral infection, and/or fungal infection, wherein the method comprises applying the antimicrobial gel of claim 13 to a patient in need thereof.

37. A method for treating a burn, scar, bacterial infection, viral infection, and/or fungal infection, wherein the method comprises applying the antimicrobial dressing of claim 30 to a patient in need thereof.

38. An antimicrobial gel comprising at least two polysiloxanes, wherein the antimicrobial gel is formed by creating at least one covalent bond between at least one an alkenyl and/or alkynyl moiety of a first polysiloxane and at least one Si—H moiety of a second polysiloxane, the antimicrobial gel further comprises at least one hydrosilylation catalyst, at least one silver salt, and at least one hydrophilic component, wherein the at least one hydrophilic component promotes release of the at least one silver salt such that the antimicrobial gel has an accumulated silver release of at least 0.3% of the total silver content in the initial antimicrobial gel after 24 hours, wherein the at least one hydrophilic component makes the antimicrobial gel swell at least 5% (wt/wt) after 24 hours in a water solution containing 8.298 g/L of sodium chloride and 0.368 g/L of calcium chloride dihydrate, as measured by the free swell absorption method.

39. The antimicrobial gel according to claim 38, wherein the at least one hydrophilic component comprises a mono-polysaccharide, di-polysaccharide, sugar alcohol, polyol, polyether, polyester, polyamide, polymer comprising a pendant carboxylic acid group, a polymer comprising a pendant sulphonate group, or a mixture thereof.

40. The antimicrobial gel of claim 38, wherein the at least one silver salt comprises $Ag_2SO_4$, $Ag_2SO_3$; $AgNO_3$, $Ag_2CO_3$, $Ag_3PO_4$, silver zirconium, silver citrate, silver acetate, silver lactate, or a mixture thereof.

41. The antimicrobial gel of claim 38, wherein the antimicrobial gel further comprises one or more excipients comprising a siloxane-containing copolymer, silica particle, or a mixture thereof.

42. The antimicrobial gel of claim 38, wherein the corrected zone of inhibition (CZoI) of microbial growth brought about by the antimicrobial gel is at least 2 mm at 24 h.

43. An antimicrobial dressing comprising the antimicrobial gel of claim 38.

44. The antimicrobial dressing of claim 43, wherein the antimicrobial gel is applied on a substrate.

45. The antimicrobial dressing of claim 43, wherein the dressing comprises a wound dressing, an ostomy dressing, ostomy baseplate, incision film, surgical drape, a patch, a bandage, a band-aid, a plaster, an adhesive, an adhesive tape, an adhesive plaster, a sticking-plaster, a court-plaster, or a combination thereof.

46. A method for preparing an antimicrobial gel of claim 38, comprising the following steps of:
(a) preparing the three mixtures (i), (ii), and (iii), either simultaneously or sequentially or in any combination of (i), (ii), and (iii), comprising;
   (i) at least one alkenyl- and/or alkynyl-functional polysiloxane, at least one hydrosilylation catalyst and, optionally, silica particles;
   (ii) at least one alkenyl- and/or alkynyl-functional polysiloxane, at least one chain extender and/or at least one crosslinker, and, optionally, silica particles;
   (iii) at least one silver salt and at least one siloxane-containing copolymer;
(b) mixing at least one hydrophilic component with mixture (i) and/or mixture (ii), followed by optionally heating the mixture(s) to which the at least one hydrophilic component was added, in order to melt the at least one silver-release enhancing hydrophilic component;
(c) mixing mixture (iii) with mixture (i) and/or mixture (ii);
(d) mixing mixture (i) and mixture (ii); and
(e) curing the mixture obtained in step (d), thereby obtaining the antimicrobial gel.

47. A method for preparing an antimicrobial dressing of claim 43, comprising the following steps of:
(a) preparing the three mixtures (i), (ii), and (iii), either simultaneously or sequentially or in any combination of (i), (ii), and (iii), comprising;
   (i) at least one alkenyl- and/or alkynyl-functional polysiloxane, at least one hydrosilylation catalyst and, optionally, silica particles;
   (ii) at least one alkenyl- and/or alkynyl-functional polysiloxane, at least one chain extender and/or at least one crosslinker, and, optionally, silica particles;

(iii) at least one silver salt and at least one siloxane-containing copolymer;

(b) mixing the at least one hydrophilic component with mixture (i) and/or mixture (ii), followed by optionally heating the mixture(s) to which the at least one hydrophilic component was added, in order to melt the hydrophilic component;

(c) mixing mixture (iii) with mixture (i) and/or mixture (ii) U;

(d) mixing mixture (i) and mixture (ii);

(e) coating a substrate with the mixture obtained in step (d); and (f) curing the mixture coated on the substrate of step (e), thereby obtaining the antimicrobial dressing.

48. The method of claim 47, wherein the substrate comprises a wound dressing, an ostomy dressing, an ostomy baseplate, an incision film, a surgical drape, a pad, a patch, a bandage, a band-aid, a plaster, an adhesive, an adhesive tape, an adhesive plaster, a sticking-plaster, a court-plaster, or a mixture thereof, or wherein the substrate is a component for production of any one of the above substrates, wherein the component for production comprises a film, a textile, a foam, a non-woven film, a fiber network, a knitted fabric, or a combination thereof.

49. A method for treating a burn, scar, bacterial infection, viral infection, and/or fungal infection, wherein the method comprises applying the antimicrobial gel of claim 38 to a patient in need thereof.

50. A method for treating a burn, scar, bacterial infection, viral infection, and/or fungal infection, wherein the method comprises applying the antimicrobial gel according of claim 38 to a patient in need thereof.

* * * * *